(12) United States Patent
Hölzemann et al.

(10) Patent No.: US 6,649,613 B1
(45) Date of Patent: Nov. 18, 2003

(54) DIACYLHYDRAZINE DERIVATIVES

(75) Inventors: Günter Hölzemann, Seeheim (DE);
Simon Goodman, Darmstadt (DE);
Horst Kessler, Schwalbach (DE);
Christoph Gibson, Munich (DE);
Gabór Sulyok, Munich (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/030,691

(22) PCT Filed: Jul. 5, 2000

(86) PCT No.: PCT/EP00/06307

§ 371 (c)(1),
(2), (4) Date: Jan. 14, 2002

(87) PCT Pub. No.: WO01/05753

PCT Pub. Date: Jan. 25, 2001

(30) Foreign Application Priority Data

Jul. 14, 1999 (DE) .......................................... 199 32 796

(51) Int. Cl.[7] ..................... C07C 243/38; A61K 31/15; A61K 31/4402; C07D 237/20; A61P 9/02
(52) U.S. Cl. ...................... 514/247; 562/439; 562/561; 544/330; 544/331; 544/238; 544/407; 544/336; 544/224; 546/264; 546/276.7; 546/306; 548/312.1; 548/326.5; 514/565; 514/252.06; 514/255.06; 514/275; 514/332; 514/339; 514/397; 514/398; 514/407

(58) Field of Search ................................. 562/439, 561; 514/565, 252.06, 247, 255.06, 275, 332, 339, 397, 398, 407; 544/330, 331, 238, 407, 336, 224; 546/264, 276.7, 306; 548/312.1, 326.5

(56) References Cited

FOREIGN PATENT DOCUMENTS

WO      WO 99/20272 A      4/1999

*Primary Examiner*—Mukund J. Shah
*Assistant Examiner*—Kahsay Habte
(74) *Attorney, Agent, or Firm*—Millen, White, Zelano, Branigan, P.C.

(57) ABSTRACT

Diacylhydrazine derivatives of general formula (I)

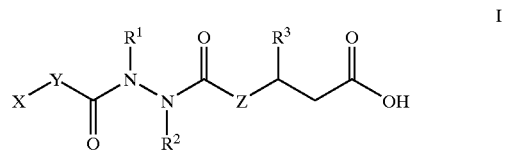

wherein X, Y, Z, $R^1$, [2] and $R^3$ are as defined herein, and their physiologically acceptable salts or solvates thereof, are integrin inhibitors and can be used to combat thromboses, myocardial infarcts, coronary cardiac diseases, arteriosclerosis, inflammations, tumors, osteoporosis, infections, and restenosis following angioplasty or during pathological processes that are maintained or propagated by angiogenesis.

35 Claims, No Drawings

DIACYLHYDRAZINE DERIVATIVES

The invention relates to diacylhydrazine derivatives of the formula I $$X-Y-\underset{O}{C}-\underset{R^1}{N}-\underset{R^2}{N}-\underset{O}{C}-Z-\underset{R^3}{CH}-CH_2-C(O)OH \quad I$$

in which

X is $H_2N-C(=NH)-NH-$, $H_3C-C(=NH)-NH-$ or $Het^1-NH-$, $-(CH_2)_n-$ or $-(CH_2)_m-\underset{R^4}{\phantom{C}\bigcirc\phantom{C}}-(CH_2)_o-$, Y is Z is $N-R^2$ or $CH-R^2$, $R^1$, $R^2$ are each independently of one another H or A, $R^3$ is H, Ar or Het, $R^4$ is H, A, Ar, OH, OA, OAr, arylalkyl, Hal, CN, $NO_2$, $CF_3$ or $OCF_3$ A is alkyl having 1 to 6 carbon atoms, Ar is phenyl which is unsubstituted or mono-, di- or trisubstituted by A, OH, OA, $CF_3$, $OCF_3$, CN, $NO_2$ or Hal and which may be substituted by a phenyl which is mono-, di- or trisubstituted by A, OH, OA, $CF_3$, $OCF_3$, CN, $NO_2$ or Hal such that an unsubstituted or substituted biphenyl is formed or naphthyl which is unsubstituted or mono-, di- or trisubstituted by A, OH, OA, $CF_3$, $OCF_3$, CN, $NO_2$ or Hal, Hal is F, Cl, Br or I, Het is a saturated, partially or fully unsaturated mono- or bicyclic heterocyclic radical having 5 to 10 ring members, wherein 1 or 2 nitrogen and/or 1 or 2 sulfur or oxygen atoms may be present and wherein the heterocyclic radical may be mono- or disubstituted by CN, Hal, OH, OA, $CF_3$, A, $NO_2$ or $OCF_3$, $Het^1$ is a 5- or 6-membered aromatic heterocycle having 1 to 4 nitrogen atoms which may be unsubstituted or mono- or disubstituted by Hal, A, OA, Ar, OAr, arylalkyl, CN, $NO_2$, $CF_3$ or $OCF_3$, n is 2, 3, 4, 5 or 6, m, o are 0, 1 or 2, and their physiologically acceptable salts and solvates.

Partially similar compounds are known from EP 0 632 016, WO 97/26250, WO 97/24124 or DE 198 31 710.

The invention was based on the object of discovering novel compounds having valuable properties, in particular those which can be used for preparing medicaments.

It has been found that the compounds of the formula I and their salts have very valuable pharmacological properties, coupled with a good tolerability. Above all, they act as integrin inhibitors, and in particular inhibit the interactions of the αv-, β3-, β5- or β6-integrin receptors with ligands, such as, for example, binding of fibrinogen to the integrin receptor.

Integrins belong to the family of heterodimeric class I—transmembrane receptors which play an important role in numerous cell-matrix or cell-cell adhesion processes (Tuckwell et al., 1996, Symp. Soc. Exp. Biol. 47). Roughly, they can be divided into three classes: the β1-integrins, which are receptors for the extracellular matrix, the β2-integrins, which are activatable on leukocytes and are triggered during inflammatory processes, and the αv-integrins, which influence the cellular response during wound healing and other pathological processes (Marshall and Hart, 1996, Semin. Cancer Biol. 7, 191). The relative affinity and specificity for ligand binding is determined by the combination of the various α- and β-subunits.

The compounds according to the invention are particularly effective in the case of the integrins αvβ1, αvβ3, αvβ5, αIIbβ3 and also αvβ6 and αvβ8, preferably of αvβ3, αvβ5 and αvβ6, and also αIIbβ3.

αvβ6 is a relatively rare integrin (Busk et al., J. Biol. Chem. 1992, 267(9), 5790) which is increasingly formed during reparation processes in epithelial tissue and which preferably binds the natural matrix molecules fibronectin and tenascin (Wang et al., Am. J. Respir. Cell Mol. Biol. 1996, 15(5), 664). The physiological and pathological functions of αvβ6 are not yet known in detail; however, it is assumed that this integrin plays an important role in physiological processes and disorders (for example inflammations, wound healing, tumours) in which epithelial cells are involved. Thus, αvβ6 is expressed on keratinocytes in wounds (Haapasalmi et al., J. Invest. Dermatol. 1996, 106(1), 42), which indicates that, in addition to wound-healing processes and inflammations, other pathological processes in the skin, such as, for example, psoriasis, bullous pemphigus, dermatitis and erythema, and also cystic fibrosis, endometriosis, cirrhosis of the liver or periodontitis, can also be influenced by agonists or antagonists of said integrin. Furthermore, αvβ6 plays a role in the epithelium of the respiratory tract (Weinacker et al., Am. J. Respir. Cell Mol. Biol. 1995, 12(5), 547) so that it may be possible to use appropriate agonists/antagonists of this integrin successfully for disorders of the respiratory tract, such as bronchitis, asthma, pulmonary fibrosis and tumours of the respiratory tract. Finally, it is known that αvβ6 also plays a role in the intestinal epithelium, so that appropriate integrin agonists/antagonists could be used for treating inflammations, tumours and wounds of the gastrointestinal tract.

It has been found that the compounds of the formula I according to the invention and their salts, as soluble molecules, act on cells carrying the receptor mentioned, or, if they are attached to surfaces, they are artificial ligands for the αvβ6-mediated cell adhesion. Especially, they act as αvβ6 integrin inhibitors, inhibiting in particular the interactions of the receptor with other ligands, such as, for example, binding of fibronectin.

In particular, the compounds according to the invention are potent inhibitors of the vitronectin receptor αvβ3 and/or potent inhibitors of the αvβ6-receptor.

The αvβ3 integrin is expressed on a number of cells, for example endothelial cells, smooth vascular muscle cells, for example of the aorta, cells which degrade the bone matrix (osteoclasts) or tumour cells.

The action of the compounds according to the invention can be demonstrated, for example, using the method described by J. W. Smith et al. in J. Biol. Chem. 1990, 265, 12267–12271.

In Curr. Opin. Cell. Biol. 1993, 5, 864, B. Felding-Habermann and D. A. Cheresh describe the importance of the integrins as adhesion receptors for various phenomena and symptoms, specifically with respect to the vitronectin receptor αvβ3.

The dependence of the formation of angiogenesis on the interaction between vascular integrins and extra-cellular matrix proteins is described by P. C. Brooks, R. A. Clark and D. A. Cheresh in Science 1994, 264, 569–671.

P. C. Brooks, A. M. Montgomery, M. Rosenfeld, R. A. Reisfeld, T. Hu, G. Klier and D. A. Cheresh describe, in Cell 1994, 79, 1157–1164 the possibility of inhibiting this interaction, thus initiating apoptosis (programmed cell death) of angiogenic vascular cells by a cyclic peptide. They describe, for example, αvβ3 antagonists or antibodies against αvβ3 which cause tumours to shrink, by initiating apoptosis.

The experimental proof that the compounds according to the invention also prevent adhesion of living cells on the corresponding matrix proteins and, accordingly, also adhesion of tumour cells to matrix proteins can be obtained in a cell adhesion test, analogously to the method of F. Mitjans et al., J. Cell Science 1995, 108, 2825–2838.

In J. Clin. Invest. 1995, 96, 1815–1822, P. C. Brooks et al. describe αvβ3 antagonists for controlling cancer and for treating tumour-induced angiogenic disorders. The compounds are capable of inhibiting binding of metal proteinases to integrins, thus preventing the cells from utilizing the enzymatic activity of the proteinase. An example is given by the inhibition of MMP-2 (matrix metalloproteinase 2) binding to the vitronectin receptor αvβ3 by a cyclo-RGD peptide, as described in P. C. Brooks et al., Cell 1996, 85, 683–693.

It is therefore possible to use the compounds of the formula I according to the invention as medicinally active compounds, in particular for treating tumour disorders, osteoporoses, osteolytic disorders, and for suppressing angiogenesis.

Compounds of the formula I which block the interaction of integrin receptors and ligands, such as, for example, of fibrinogen on the fibrinogen receptor (glycoprotein IIb/IIIa), inhibit, as GPIIb/IIIa antagonists, the spreading of tumour cells by metastasis. This is demonstrated by the following observations:

tumour cells spread from a localized tumour into the vascular system by forming microaggregates (microthrombi) by interaction of the tumour cells with platelets. Protected in the microaggregate, the tumour cells are shielded and are not recognized by the cells of the immune system. These microaggregates can establish themselves at the walls of blood vessels, thus facilitating further penetration of tumour cells into the tissue. Since the formation of the microthrombi is mediated by fibrinogen binding to the fibrinogen receptors on activated platelets, the GPIIb/IIIa antagonists can be considered to be effective metastasis inhibitors.

In addition to binding of fibrinogen, fibronectin and the von-Willebrand factor to the platelet fibrinogen receptor, compounds of the formula I also inhibit binding of further adhesive proteins, such as vitronectin, collagen and laminin, to the corresponding receptors on the surface of various cell types. In particular, they inhibit the formation of platelet thrombi and can therefore be used for treating thromboses, apoplexy, myocardial infarction, inflammations and arteriosclerosis.

The inhibitory effect on thrombocyte aggregation can be demonstrated in vitro using the method of Born (Nature 1962, 4832, 927–929).

A measure for the uptake of a medicinally active compound into an organism is its bioavailability.

If the medicinally active compound is administered to the organism intravenously, in the form of a solution for injection, its absolute bioavailability, i.e. the percentage of the pharmaceutical which enters the systemic circulation unchanged, i.e. the greater circulation, is 100%.

If a therapeutically active compound is administered orally, the active compound is generally present in the formulation as a solid and, accordingly, first has to pass into solution to be able to overcome the entry barriers, for example the gastrointestinal tract, the mucosa of the mouth, nasal membranes or the skin, in particular the stratum corneum, or to be resorbed by the body. Pharmacokinetic data, i.e. data on the bioavailability, can be obtained analogously to the method of J. Shaffer et al, J. Pharm. Sciences, 1999, 88, 313–318.

The invention provides compounds of the formula I according to claim 1 and their physiologically acceptable salts and/or solvates for use as therapeutically active compounds.

Accordingly, the invention provides compounds of the formula I according to claim 1 and their physiologically acceptable salts and/or solvates for use as integrin inhibitors.

The invention provides compounds of the formula I according to claim 1 and their physiologically acceptable salts and/or solvates for use in the control of diseases.

The compounds of the formula I can be employed as medicinally active compounds in human and veterinary medicine, in particular for the prophylaxis and/or therapy of cardiovascular disorders, thrombosis, myocardial infarction, arteriosclerosis, apoplexy, angina pectoris, tumour diseases, such as tumour growth or tumour metastasis, osteolytic diseases, such as osteoporosis, pathological angiogenic diseases, such as, for example, inflammations, ophthalmological diseases, diabetic retinopathy, macular degeneration, myopia, ocular histoplasmosis, rheumatoid arthritis, osteoarthritis, rubeotic glaucoma, ulcerative colitis, Crohn's disease, atherosclerosis, psoriasis, bullous pemphigus, dermatitis, erythema, pulmonary fibrosis, cystic fibrosis, endometriosis, cirrhosis of the liver, periodontitis, restenosis after angioplasty, multiple sclerosis, viral infection, bacterial infection, fungal infection, in cases of acute renal failure and in cases of wound healing to assist the healing process.

The compounds of the formula I can be employed as antimicrobially acting substances during operations where biomaterials, implants, catheters or cardiac pacemakers are used.

Here, they have an antiseptic action. The efficacy of the antimicrobial activity can be demonstrated by the method described by P. Valentin-Weigund et al. in Infection and Immunity, 1988, 2851–2855.

Since the compounds of the formula I are inhibitors of fibrinogen binding and thus ligands of the fibrinogen receptors on platelets, they can be used as diagnostic aids for the, detection and localization of thrombi in the vascular system in vivo if they are substituted, for example, by a radioactive or UV-detectable radical.

As inhibitors of fibrinogen binding, the compounds of the formula I can also be employed as effective auxiliaries for the study of the metabolism of platelets in different activation stages or of intracellular signal mechanisms of the fibrinogen receptor. The detectable unit of a "label" which is to be incorporated, for example isotope labelling by $^3$H, permits the investigation of the abovementioned mechanisms after receptor binding.

The following abbreviations are used:

| | |
|---|---|
| Ac | acetyl |
| Aza-Gly | H₂N—NH—COOH |
| BOC | tert-butoxycarbonyl |
| CBZ or Z | benzyloxycarbonyl |
| DCCI | dicyclohexylcarbodiimide |
| DCM | dichloromethane |
| DIPEA | diisopropylethylamine |
| DMF | dimethylformamide |
| EDCI | N-ethyl-N,N'-(dimethylaminopropyl)carbodiimide |
| Et | ethyl |
| Fmoc | 9-fluorenylmethoxycarbonyl |
| Gly | glycine |
| HATU | O-(7-azabenzotriazol-1-yl)-N,N,N',N'-tetramethyluronium hexafluorophosphate |
| HOBt | 1-hydroxybenzotriazole |
| Me | methyl |
| MBHA | 4-methylbenzhydrylamine |
| Mtr | 4-methoxy-2,3,6-trimethylphenylsulfonyl |
| NMP | N-methylpyrrolidone |
| NMR | nuclear magnetic resonance |
| HONSu | n-hydroxysuccinimide |
| OBzl | benzyl ester |
| OtBu | tert-butyl ester |
| Oct | octanoyl |
| OMe | methyl ester |
| OEt | ethyl ester |
| Pbf | 2,2,4,6,7-pentamethyldihydrobenzofuran-5-sulfonyl |
| β-Phe | β-phenylalanine |
| POA | phenoxyacetyl |
| R$_f$ value | retention factor |
| RP | reversed phase |
| RT | retention time |
| Sal | salicyloyl |
| TBTU | O-(1H-benzotriazol-1-yl)-N,N,N',N'-tetramethyluronium tetrafluoroborate |
| TFA | trifluoroacetic acid |
| Trt | trityl (triphenylmethyl). |

The compounds of the formula I have at least one chiral centre and can therefore be present in a plurality of stereoisomeric forms. All of these forms (for example D- and L-forms) and their mixtures (for example the DL forms) are embraced by the formula I.

The compounds according to the invention of claim 1 also include so-called prodrug derivatives, i.e. compounds of the formula I which are derivatized with, for example, alkyl or acyl groups, sugars or oligopeptides and which are rapidly cleaved in the organism to the active compounds according to the invention.

These also include biodegradable polymer derivatives of the compounds according to the invention, as described, for example, in Int. J. Pharm. 1995, 115, 61–67.

The compounds according to the invention of claim 1 also include derivatives of the compounds of the formula I whose carboxyl group has been converted into a pharmaceutically acceptable metabolically labile ester or an amide.

Furthermore, free amino groups or free hydroxyl groups as substituents of compounds of the formula I may carry appropriate protective groups.

Solvates of the compounds of the formula I are understood to be addition compounds of the compounds of the formula I with inert solvent molecules, which are formed owing to their mutual attraction. Examples of solvates are mono- or dihydrates or adducts with alcohols, such as, for example, with methanol or ethanol.

The invention furthermore provides a process for preparing compounds of the formula I according to claim 1 and their salts, characterized in that a) to prepare a compound of the formula I in which Z is N—R², a compound of the formula II

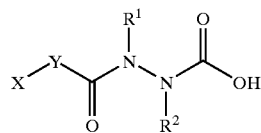

in which X, Y, R¹ and R² are as defined in claim 1 and in which free amino groups are protected by a suitable amino protective group,
is reacted with a compound of the formula III

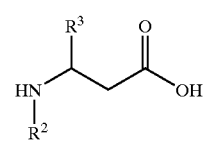

in which R² and R³ are as defined in claim 1 and in which a free hydroxyl group is protected by a suitable hydroxyl protective group or attached to a solid phase,
and the protective groups and/or the solid phase are subsequently removed, or b) a compound of the formula IV

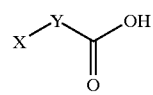

in which X and Y are as defined in claim 1 and in which free amino groups are protected by a suitable amino protective group
is reacted with a compound of the formula V

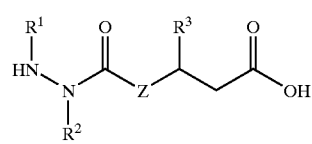

in which R¹, R², R³ and Z are as defined in claim 1 and in which a free hydroxyl group is protected by a suitable hydroxyl protective group or attached to a solid phase,
and the protective groups and/or the solid phase are subsequently removed;

or c) a compound of the formula I is liberated from one of its functional derivatives by treatment with a solvolysing or hydrogenolysing agent,
and/or in that a basic or acidic compound of the formula I is converted into one of its salts by treatment with an acid or base.

For the entire invention, it applies that all radicals which are present more than once, such as, for example, R², can be identical or different, i.e. are independent of one another.

In the above formulae, A is alkyl which is linear or branched and has 1 to 6, preferably 1, 2, 3, 4, 5 or 6, carbon atoms. A is preferably methyl, furthermore ethyl, isopropyl, n-propyl, n-butyl, isobutyl, sec-butyl or tert-butyl, furthermore also n-pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

A is particularly preferably methyl.

Amino protective group is preferably acetyl, propionyl, butyryl, phenylacetyl, benzoyl, toluoyl, POA, methoxycarbonyl, ethoxycarbonyl, 2,2,2-trichloroethoxycarbonyl, BOC, 2-iodoethoxycarbonyl, CBZ ("carbobenzoxy"), 4-methoxybenzyloxycarbonyl, Fmoc, Mtr or benzyl.

Fmoc is particularly preferred.

Ar is preferably unsubstituted phenyl, furthermore preferably phenyl which is mono-, di- or trisubstituted by A, OH, OA, $CF_3$, $OCF_3$, CN, $NO_2$ or Hal and which may also be substituted by a phenyl which is mono-, di- or trisubstituted by A, OH, OA, $CF_3$, $OCF_3$, CN, $NO_2$ or Hal such that an unsubstituted or substituted biphenyl is formed. A and Hal have the preferred or particularly preferred meanings listed above or below.

Ar is furthermore preferably unsubstituted naphthyl or naphthyl which is mono-, di- or trisubstituted by A, OH, OA, $CF_3$, $OCF_3$, CN, $NO_2$ or Hal, where A and Hal have one of the preferred or particularly preferred meanings listed above or below.

Accordingly, Ar is preferably phenyl, o-, m- or p-methylphenyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-methoxyphenyl, o-, m- or p-ethoxyphenyl, o-, m-, p-trifluoromethylphenyl, o-, m-, p-trifluoromethoxyphenyl, o-, m- or p-fluorophenyl, o-, m- or p-chlorophenyl, o-, m- or p-bromophenyl, o-, m-, p-nitrophenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-dimethoxyphenyl, 2,3-, 2,4-, 2,5-, 2,6-, 3,4- or 3,5-dihydroxyphenyl, 2,3-, 2,4-, 2,5-, 2,6-, 3,4- or 3,5-ditrifluoromethylphenyl, 2,3-, 2,4-, 2,5-, 2,6-, 3,4- or 3,5-ditrifluoromethoxyphenyl, 2,3-, 2,4-, 2,5-, 2,6-, 3,4- or 3,5-dinitrophenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl. However, preference is furthermore also given to unsubstituted biphenyl or else substituted biphenyl, specifically preferably to 4-biphenyl or 3-biphenyl, 4'-(2-methylbiphenyl), 4'-(3-methylbiphenyl), 4'-(4-methylbiphenyl), 3'-(2-methylbiphenyl), 3'-(3-methylbiphenyl), 3'-(4-methylbiphenyl), 4-(2-methylbiphenyl), 4-(3-methylbiphenyl), 3-(2-methylbiphenyl), 3-(4-methylbiphenyl), 4'-(2-fluorobiphenyl), 4'-(3-fluorobiphenyl), 4'-(4-fluorobiphenyl), 31-(2-fluorobiphenyl), 3'-(3-fluorobiphenyl), 3'-(4-fluorobiphenyl), 4-(2-fluorobiphenyl), 4-(3-fluorobiphenyl), 3-(2-fluorobiphenyl) or 3-(4-fluorobiphenyl).

However, preference is furthermore also given to unsubstituted naphthalin-1-yl or napthalin-2-yl.

Ar is particularly preferably phenyl, p-chlorophenyl, p-bromophenyl, p-fluorophenyl, 3,5-dichlorophenyl, o- or m-nitrophenyl, p-trifluoromethoxyphenyl, p-methoxyphenyl, 3,5-dichloro-2-hydroxyphenyl, naphthalin-1-yl, biphenyl-4-yl or 4'-(4-fluorobiphenyl).

Aralkyl is preferably benzyl, phenylethyl, phenylpropyl or naphthylmethyl, particularly preferably benzyl.

Hal is preferably F, Cl or Br.

Het is a saturated, partially or fully unsaturated mono- or bicyclic heterocyclic radical having 5 to 10 ring members, wherein 1 or 2 nitrogen and/or 1 or 2 sulfur or oxygen atoms may be present and the heterocyclic radical may be mono- or disubstituted by CN, Hal, OH, OA, $CF_3$, A, $NO_2$ or $OCF_3$.

Het is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or -5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzthiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl. The heterocyclic radicals can also be partially or fully hydrogenated. Het can therefore also be 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -3-pyrolyl, tetrahydro-1-, -2- or 4-imidazolyl, 2,3-dihydro-1-, -2-, -3-, -4-, -5-, -6-, -7-1H-indolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 1-, 2-, 3- or 4-azepanyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolinyl, 1,2,3,4-tetrahydro-1-, -2-, -3-, -4-, -5-, -6-, -7- or -8-isoquinolinyl.

Het is particularly preferably 2-, 3- or 4-pyridyl or 1-, 2-, 3-, 4-, 5-, 6- or 7-1H-indolyl.

$Het^1$ is a 5- or 6-membered aromatic heterocycle having 1 to 4 nitrogen atoms which may be unsubstituted or mono- or disubstituted by Hal, A, OA, Ar, OAr, arylalkyl, CN, $NO_2$, $CF_3$ or $OCF_3$, wherein Hal, A, arylalkyl and Ar have one of the meanings given above.

$Het^1$ is preferably unsubstituted or substituted 2- or 3-pyrrolyl, 2, 4- or 5-imidazolyl, 3-, 4- or 5-pyrazolyl, 2-, 3- or 4-pyridyl, 2-, 4-, 5- or 6-pyrimidinyl, 3- or 4-pyridazinyl, 2- or 3-pyrazinyl. Particular preference is given to pyridin-2-yl, imidazol-2-yl or 4-methylpyridin-2-yl.

$Het^1$—NH is preferably pyrrol-2- or pyrrol-3-ylamine, imidazol-2-, imidazol-4- or imidazol-5-ylamine, pyrazol-3-, pyrazol-4- or pyrazol-5-ylamine, pyrid-2-, pyrid-3- or pyrid-4-ylamine, pyrimidin-2-, pyrimidin-4-, pyrimidin-5- or pyrimidin-6-ylamine, pyridazin-3- or pyridazin-4-ylamine, pyrazin-2- or pyrazin-3-ylamine, where the heterocyclic rings mentioned may be substituted, preferably by alkyl. $Het^1$—NH is particularly preferably pyrid-2-ylamine, imidazol-2-ylamine or 4-methylpyridin-2-ylamine.

OA is preferably methoxy, ethoxy, propoxy or butoxy, furthermore also pentyloxy or hexyloxy.

$R^1$ is preferably H or A, where A has one of the meanings given above, and is in particular H.

$R^2$ is preferably H or A, where A has one of the meanings given above, and is in particular H.

$R^3$ is preferably H, Ar or Het, where Ar and Het have one of the meanings given above, and is in particular H, phenyl, p-chlorophenyl, p-bromophenyl, p-fluorophenyl, 3,5-dichlorophenyl, o- or m-nitrophenyl, p-trifluoromethoxyphenyl, p-methoxyphenyl, 3,5-dichloro-2-hydroxyphenyl, naphthalin-1-yl, biphenyl-4-yl or 4'-(4-fluorobiphenyl).

$R^4$ is preferably H, A, Ar, OH, OA, OAr, arylalkyl, Hal, CN, $NO_2$, $CF_3$ or $OCF_3$, wherein A, arylalkyl, Ar and Hal have one of the meanings given above, and is in particular H and methyl.

X is $H_2N$—C(=NH)—NH—, $H_3C$—C(=NH)—NH— or $Het^1$—NH wherein $Het^1$—NH has one of the meanings given above, and in particular, X is $H_2N$—C(=NH)—NH—, $H_3C$—C(=NH)—NH—, pyridin-2-ylamino, imidazol-2-ylamino or 4-methylpyridin-2-ylamino.

Y is —$(CH_2)_n$— or

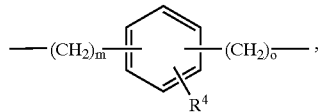

wherein n is 2, 3, 4, 5 or 6, in particular 3 or 4, and m is 0, 1 or 2, in particular 0, and o is 0, 1 or 2, in particular 0 or 1, and $R^4$ has one of the meanings given above.

Z is N—$R^2$ or CH—$R^2$, wherein $R^2$ has one of the meanings given above, and is in particular NH or $CH_2$.

Accordingly, the invention provides in particular those compounds of the formula I in which at least one of the radicals mentioned has one of the preferred meanings given above. Some preferred groups of compounds can be expressed by the following partial formulae Ia to Ir which correspond to the formula I and in which the radicals that are not specified in more detail are as defined under formula I, but in which in Ia) X is $H_2N$—C(=NH)—NH—, in Ib) Y is

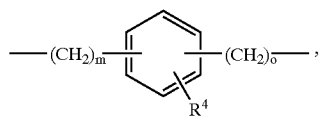

in Ic) Z is N—$R^2$,
in Id) Z is CH—$R^2$,
in Ie) X is $H_2N$—C(=NH)—NH—, $H_3C$—C(=NH)—NH— or $Het^1$—NH— and
Y is —$(CH_2)_n$,
in If) X is $H_2N$—C(=NH)—NH— and
Y is

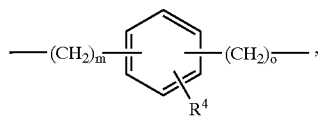

in Ig) X is $H_2N$—C(=NH)—NH— or $Het^1$—NH—,
Y is —$(CH_2)_n$—,
$R^3$ is Ar,
Z is NH, in Ih) X is $H_2N$—C(=NH)—NH—,
$R^3$ is Ar,
Z is NH and
Y is

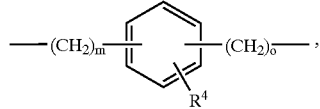

in Ii) X is $H_2N$—C(=NH)—NH— or $Het^1$—NH—,
$R^3$ is Ar,
Y is —$(CH_2)_n$— and
Z is $CH_2$,
in Ik) X is $H_2N$—C(=NH)—NH—,
$R^3$ is Ar,
Z is $CH_2$ and
Y is

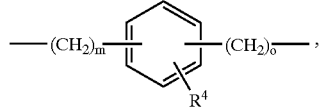

in Im) X is $H_2N$—C(=NH)—NH—, $H_3C$—C(=NH)—NH— or $Het^1$—NH—,
Y is —$(CH_2)_n$— or

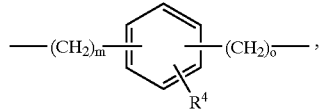

Z is NH or $CH_2$
$R^1$, $R^2$ are H,
$R^3$ is Ar,
$R^4$ is H,
$Het^1$ is 4-methylpyridin-2-yl, pyridin-2-yl or imidazol-2-yl,
n is 3 or 4,
m is 0 and
o is 0 or 1,
in In) X is $H_2N$—C(=NH)—NH— or $Het^1$—NH—,
Y is —$(CH_2)_n$— or

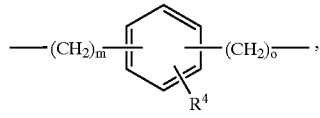

Z is NH
$R^1$, $R^2$ are H,
$R^3$ is phenyl which is unsubstituted or mono-, di- or trisubstituted by OH, OA, $OCF_3$, $NO_2$ or Hal and which may be substituted by a phenyl which is unsubstituted or mono-, di- or trisubstituted by Hal such that an unsubstituted or substituted biphenyl is formed or unsubstituted naphthyl,
$R^4$ is H,
$Het^1$ is 4-methylpyridin-2-yl, or pyridin-2-yl or imidazol-2-yl,
n is 3 or 4 and
m is 0 and
0 is 0 or 1, in Io) X is H$_2$N—C(=NH)—NH— or Het$^1$—NH—,
Y is —(CH$_2$)$_n$— or

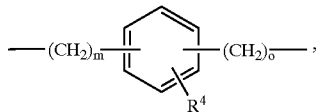

Z is CH$_2$,
R$^1$, R$^2$ are H,
R$^4$ is H,
R$^3$ is phenyl which is unsubstituted or mono-, di- or trisubstituted by OH, OA, OCF$_3$, NO$_2$ or Hal and which may be substituted by a phenyl which is unsubstituted or mono-, di- or trisubstituted by Hal such that an unsubstituted or substituted biphenyl is formed or unsubstituted naphthyl,
Het$^1$ is 4-methylpyridin-2-yl, pyridin-2-yl or imidazol-2-yl,
n is 4 and
m, o are 0,
in Ip) X is H$_2$N—C(=NH)—NH— or Het$^1$—NH—,
Y is —(CH$_2$)$_n$— or

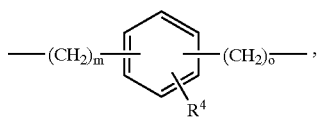

Z is NH or CH$_2$,
R$^1$, R$^2$ are H,
R$^4$ is H,
R$^3$ is phenyl which is unsubstituted or mono-, di- or trisubstituted by OH, OA, OCF$_3$, NO$_2$ or Hal and which may be substituted by a phenyl which is unsubstituted or mono-, di- or trisubstituted by Hal such that an unsubstituted or substituted biphenyl is formed or unsubstituted naphthyl,
Het$^1$ is 4-methylpyridin-2-yl, pyridin-2-yl or imidazol-2-yl,
n is 3 or 4,
m is 0 and
o is 0 or 1,
in Iq) R$^3$ is unsubstituted biphenyl-4-yl or is phenyl which is mono-, di- or trisubstituted by Hal,
in Ir) X is H$_2$N—C(=NH)—NH— or Het$^1$—NH—,
Y is —(CH$_2$)$_n$— or

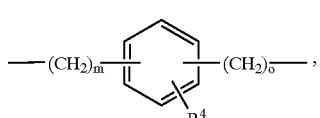

Z is NH or CH$_2$,
R$^1$, R$^2$ are H,
R$^4$ is H,
R$^3$ is biphenyl-4-yl, 4-chlorophenyl or 3,5-dichlorophenyl,
Het$^1$ is 4-methylpyridin-2-yl, pyridin-2-yl or imidazol-2-yl,
n is 3 or 4,
m is 0 and
o is 0 or 1.

The compounds of the formula I and also the starting materials for their preparation are otherwise prepared by methods known per se, such as are described in the literature (for example in the standard works, such as Houben-Weyl, Methoden der organischen Chemie [Methods of organic chemistry], Georg-Thieme-Verlag, Stuttgart), and more specifically under reaction conditions which are known and suitable for the reactions mentioned. In these reactions, variants which are known per se and are not mentioned here in more detail can also be employed.

If desired, the starting materials can also be formed in situ, so that they are not isolated from the reaction mixture but are immediately reacted further to give the compounds of the formula I.

Compounds of the formula I can preferably be obtained under the conditions of a peptide synthesis. It is advantageous to employ customary methods of peptide synthesis, as described, for example, in Houben-Weyl, l.c., Volume 15/II, pages 1 to 806 (1974).

The direct precursors of the compounds of the formula I can also be synthesized on a solid phase, for example a swellable polystyrene resin, for example according to Merrifield (Angew. Chem. 97, 801–812, 1985). Suitable for use as solid phase are, in principle, all supports as known, for example, from solid-phase peptide chemistry or nucleic acid synthesis.

Suitable polymeric support materials are polymeric solid phases preferably having hydrophilic properties, for example crosslinked polysugars, such as cellulose, sepharose or Sephadex®, acrylamides, polymers based on polyethylene glycols or Tentakelpolymere®. The solid phase used is preferably trityl chloride polystyrene resin, 4-methoxytrityl chloride resin, Merrifield resin and Wang resin.

Thus, compounds of the formula I can be obtained by reacting a compound of the formula II with a compound of the formula III, followed by removal of the protective groups or the solid phase.

It is also possible to obtain the compounds of the formula I by reacting a compound of the formula IV with a compound of the formula V, followed by removal of the protective groups.

The coupling reaction is preferably carried out in the presence of a dehydrating agent, for example a carbodiimide such as DCCI or EDCI, furthermore, for example, propanephosphonic anhydride (cf. Angew. Chem. 1980, 92, 129), diphenylphosphoryl azide or 2-ethoxy-N-ethoxycarbonyl-1,2-dihydroquinoline, in an inert solvent, for example a halogenated hydrocarbon such as dichloromethane, in an ether such as tetrahydrofuran or dioxane, in an amide such as DMF or dimethylacetamide, in a nitrile such as acetonitrile, in dimethyl sulfoxide or in the presence of these solvents, at temperatures between approximately –10 and 40, preferably between 0 and 30°. It is advantageous to work in dilute solutions to promote intramolecular cyclization rather than intermolecular peptide formation.

Depending on the conditions employed, the reaction time is between some minutes and 14 days.

Instead of compounds of the formula II and/or IV, it is also possible to employ derivatives of compounds of the formula II and/or IV, preferably a pre-activated carboxylic acid, or a carbonyl halide, a symmetric or mixed anhydride or an activated ester. Such radicals for the activation of the carboxyl group in typical acylation reactions are described in the literature (for example in the standard works such as Houben-Weyl, Methoden der organischen Chemie, Georg-Thieme-Verlag, Stuttgart).

Activated esters are advantageously formed in situ, for example by addition of HOBt or N-hydroxysuccinimide.

The reaction is generally carried out in an inert solvent, if a carbonyl halide is used in the presence of an acid binder, preferably of an organic base, such as triethylamine, dimethylaniline, pyridine or quinoline.

It may also be favourable to add an alkali metal or alkaline earth metal hydroxide, carbonate or bicarbonate, or another salt of a weak acid of the alkali metals or alkaline earth metals, preferably of potassium, sodium, calcium or caesium.

The compounds of the formula I can furthermore be obtained by liberating them from their functional derivatives by solvolysis, in particular hydrolysis, or by hydrogenolysis.

Preferred starting materials for the solvolysis or hydrogenolysis are those which otherwise correspond to the formula I but, instead of one or more free amino and/or hydroxyl groups, contain corresponding protected amino and/or hydroxyl groups, in particular those which, instead of an H—N group, carry a $PG^1$-N group, in which $PG^1$ is an amino protective group, and/or those which, instead of the H atom of a hydroxyl group, carry a hydroxyl protective group, for example those which correspond to the formula I but carry, instead of a group —COOH, a group —COOPG$^2$, in which $PG^2$ is a hydroxyl protective group.

It is also possible for several—identical or different—protected amino and/or hydroxyl groups to be present in the molecule of the starting material. If the protective groups present differ from one another, in many cases they can be split off selectively (cf.: T. W. Greene, P. G. M. Wuts, *Protective Groups in Organic Chemistry*, 2nd Ed., Wiley, New York 1991 or P. J. Kocienski, Protecting Groups, 1st Ed., Georg Thieme Verlag, Stuttgart—New York, 1994, H. Kunz, H. Waldmann in *Comprehensive Organic Synthesis*, Vol. 6 (Eds. B. M. Trost, I. Fleming, E. Winterfeldt), Pergamon, Oxford, 1991, pages 631–701).

The term "amino protective group" is generally known and relates to groups which are suitable for protecting (blocking) an amino group from chemical reactions. Typical such groups are, in particular, unsubstituted or substituted acyl, aryl, aralkoxymethyl or aralkyl groups. Since the amino protective groups are removed after the desired reaction (or reaction sequence), their nature and size is otherwise not critical; however, those having 1–20 carbon atoms are preferred. The term "acyl group" is to be interpreted in the broadest sense in connection with the present process. It includes acyl groups derived from aliphatic, araliphatic, aromatic or heterocyclic carboxylic acids or sulfonic acids, and in particular alkoxycarbonyl, alkenyloxycarbonyl, aryloxycarbonyl and, above all, aralkoxycarbonyl groups. Examples of such acyl groups are alkanoyl, such as acetyl, propionyl, butyryl; aralkanoyl, such as phenylacetyl; aroyl, such as benzoyl or toluoyl; aryloxyalkanoyl, such as phenoxyacetyl; alkoxycarbonyl, such as methoxycarbonyl, ethoxycarbonyl, 2,2,2-trichloroethoxycarbonyl, Boc, 2-iodoethoxycarbonyl; alkenyloxycarbonyl, such as allyloxycarbonyl (Aloc), aralkyloxycarbonyl such as CBZ (synonymous with Z), 4-methoxybenzyloxycarbonyl (MOZ), 4-nitrobenzyloxycarbonyl or 9-fluorenylmethoxycarbonyl (Fmoc); 2-(phenylsulfonyl)ethoxycarbonyl; trimethylsilylethoxycarbonyl (Teoc), or arylsulfonyl, such as 4-methoxy-2,3,6-trimethylphenylsulfonyl (Mtr). Preferred amino protective groups are Boc, Fmoc and Aloc, furthermore Z, benzyl and acetyl.

The term "hydroxyl protective group" is also generally known and relates to groups which are suitable for protecting a hydroxyl group from chemical reactions. Typical such groups are the abovementioned unsubstituted or substituted aryl, aralkyl, aroyl or acyl groups, and furthermore also alkyl groups, alkyl-, aryl- or aralkylsilyl groups or O,O- or O,S-acetals. The nature and size of the hydroxyl protective groups are not critical, since they are removed again after the desired chemical reaction or reaction sequence; preference is given to groups having 1–20, in particular 1–10, carbon atoms. Examples of hydroxyl protective groups are, inter alia, aralkyl groups, such as benzyl, 4-methoxybenzyl or 2,4-dimethoxybenzyl, aroyl groups, such as benzoyl or p-nitrobenzoyl, acyl groups, such as acetyl or pivaloyl, p-toluenesulfonyl, alkyl groups, such as methyl or tert-butyl, but also allyl, alkylsilyl groups, such as trimethylsilyl (TMS), triisopropylsilyl (TIPS), tert-butyldimethylsilyl (TBS) or triethylsilyl, trimethylsilylethyl, aralkylsilyl groups, such as tert-butyldiphenylsilyl (TBDPS), cyclic acetals, such as isopropylidene, cyclopentylidene, cyclohexylidene, benzylidene, p-methoxybenzylidene or o,p-dimethoxybenzylidene acetal, acyclic acetals, such as tetrahydropyranyl (Thp), methoxymethyl (MOM), methoxyethoxymethyl (MEM), benzyloxymethyl (BOM) or methylthiomethyl (MTM). Particularly preferred hydroxyl protective groups are benzyl, acetyl, tert-butyl and TBS.

The liberation of the compounds of the formula I from their functional derivatives is, for the protective group employed in each case, known from the literature (for example T. W. Greene, P. G. M. Wuts, *Protective Groups in Organic Chemistry*, 2nd Ed., Wiley, New York, 1991 or P. J. Kocienski, *Protecting Groups*, 1st Ed., Georg Thieme Verlag, Stuttgart—New York, 1994). It is also possible to employ variants known per se which are not mentioned in more detail here.

A base of the formula I can be converted into the associated acid addition salt using an acid, for example by reaction of equivalent amounts of the base and the acid in an inert solvent, such as ethanol, and subsequent evaporation. Acids which give physiologically acceptable salts are particularly suitable for this reaction. It is thus possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, benzenesulfonic acid, trimethoxybenzenesulfonic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose 1-phosphate, naphthalenemono- and -disulfonic acids, or lauryl sulfuric acid. Salts with physiologically unacceptable acids, for example picrates, can be used to isolate and/or purify the compounds of the formula I. On the other hand, compounds of the formula I can be converted with bases (for example sodium hydroxide or potassium hydroxide or sodium carbonate or potassium carbonate) into the corresponding metal, in particular alkali metal or alkaline earth metal, or into the corresponding ammonium salts. Suitable salts are furthermore substituted ammonium salts, for example the dimethyl-, diethyl- or diisopropylammonium salts, monoethanol-, diethanol- or diisopropylammonium salts, cyclohexyl-, dicyclohexylammonium salts, dibenzylethylenediammonium salts, furthermore, for example, salts with arginine or lysine.

The invention furthermore provides the use of the compounds of the formula I and/or their pharmaceutically acceptable salts for preparing a pharmaceutical preparation.

The invention furthermore provides pharmaceutical preparations comprising at least one compound of the formula I and/or one of its physiologically acceptable salts or solvates prepared, in particular, by a non-chemical route. For this purpose, the compounds of the formula I can be brought into a suitable dosage form together with at least one solid, liquid and/or semiliquid excipient or auxiliary, and, if appropriate, in combination with one or more further active compounds.

These preparations can be used as medicaments in human or veterinary medicine. Possible excipients are organic or inorganic substances which are suitable for enteral (for example oral), parenteral or topical administration and which do not react with the novel compounds, for example water, vegetable oils, benzyl alcohols, alkylene glycols, polyethylene glycols, glycerol triacetate, gelatin, carbohydrates, such as lactose or starch, magnesium stearate, talc and petroleum jelly. Tablets, pills, coated tablets, capsules, powders, granules, syrups, juices or drops are used, in particular, for oral administration, suppositories are used for rectal administration, solutions, preferably oily or aqueous solutions, and furthermore suspensions, emulsions or implants, are used for parenteral administration, and ointments, creams or powders are used for topical administration. The novel compounds can also be lyophylized and the resulting lyophylizates can be used, for example, for the production of injection preparations. The preparations mentioned can be sterilized and/or comprise auxiliaries, such as lubricants, preservatives, stabilizers and/or wetting agents, emulsifiers, salts for influencing the osmotic pressure, buffer substances, dyes, flavourings and/or several other active compounds, for example one or more vitamins.

For administration as an inhalation spray, it is possible to use sprays which contain the active compound either dissolved or suspended in a propellant or propellant mixture (for example $CO_2$ or chlorofluorocarbons). Here, the active compound is expediently employed in micronized form, wherein one or more additional physiologically acceptable solvents may be present, for example ethanol. Solutions for inhalation can be administered with the aid of customary inhalators.

The compounds of the formula I and their physiologically acceptable salts can be employed as integrin inhibitors for controlling diseases, in particular thromboses, myocardial infarction, coronary heart diseases, arteriosclerosis, tumours, osteoporosis, inflammations and infections.

The compounds of the formula I according to claim 1 and/or their physiologically acceptable salts are also used for pathological processes which are maintained or propagated by angiogenesis, in particular for tumours or rheumatoid arthritis.

For this purpose, the substances according to the invention are generally preferably administered in dosages between approximately 0.05 and 500 mg, in particular between 0.5 and 100 mg, per dosage unit, analogously to other known, commercially available peptides, and in particular analogously to the compounds described in U.S. Pat. No. 4,472,305. The daily dosage is preferably between approximately 0.01 and 2 mg/kg of body weight. However, the specific dose for each patient depends on the most diverse factors, for example on the activity of the specific compound employed, on the age, body weight, general state of health, sex, on the diet, on the administration time and route, and on the rate of excretion, medicament combination and severity of the particular disease to which the therapy applies. Parenteral administration is preferred.

The compounds of the formula I can furthermore be employed as integrin ligands for preparing affinity chromatography columns for the preparation of pure integrins.

To this end, the ligand, that is to say a compound of the formula I, is covalently coupled to a polymer support via an anchor function, for example the carboxyl group of Asp.

The affinity chromatography materials for the purification of integrin are prepared under conditions like those which are customary for the condensation of amino acids and known per se.

The compounds of the formula I contain one or more chiral centres and may therefore be present in racemic or optically active form. Racemates that are obtained can be separated into the enantiomers by methods which are known per se, mechanically or chemically. Preferably, the racemic mixture is converted into diastereomers by reaction with an optically active resolving agent. Suitable resolving agents are, for example, optically active acids, such as the D and L forms of tartaric acid, diacetyltartaric acid, dibenzoyltartaric acid, mandelic acid, malic acid, lactic acid or the different optically active camphorsulfonic acids, such as β-camphorsulfonic acid. Also advantageous is an enantiomer separation with the aid of a column filled with an optically active resolving agent (for example dinitrobenzoylphenylglycine); a suitable mobile phase is, for example, a hexane/isopropanol/acetonitrile mixture, for example in a ratio by volume of 82:15:3.

It is of course also possible to obtain optically active compounds of the formula I by the methods described above by using starting materials which are already optically active.

All temperatures above and below are given in ° C. In the following examples, "customary work-up" means: water is added, if necessary, the pH is brought to values of between 2 and 10, if necessary, depending on the structure of the end product, the mixture is extracted with ethyl acetate or dichloromethane, the organic phase is separated off, dried over sodium sulfate and evaporated and the residue is purified by silica gel chromatography and/or crystallization.

RT=retention time (minutes) for HPLC in the following systems:

Columns from Omnicrom YMC:

1. 4.6×250 mm, 5 $\mu$m, $C_{18}$ (for analysis);
2. 30×250 mm, 7 $\mu$m, $C_{18}$ (for preparations).

The mobile phases used were gradients of acetonitrile (B) with 0.1% TFA and water (A) with 0.1% TFA (data in each case in per cent by volume of acetonitrile). The retention time RT was determined at a flow rate of 1 ml/min.

Detection at 220 nm.

The diastereomers are preferably separated under the given conditions.

Mass spectrometry (MS): ESI (electron spray ionization); $(M+H)^+$; FAB (fast atom bombardment); $(M+H)^+$.

EXAMPLE 1

1. 5-(9H-Fluoren-9-ylmethoxy)-3H-[1,3,4] oxadiazol-2-one 2 equivalents of phosgene (1.89M in toluene; 4.2 ml) are added to a solution of 3.91 mmol of 9H-fluoren-9-ylmethyl hydrazinecarboxylate in 40 ml of dichloromethane and 40 ml of saturated aqueous $NaHCO_3$ solution. The mixture is stirred for 15 minutes and then worked up as usual, giving 5-(9H-fluoren-9-ylmethoxy)-3H-[1,3,4]oxadiazol-2-one ("AB")

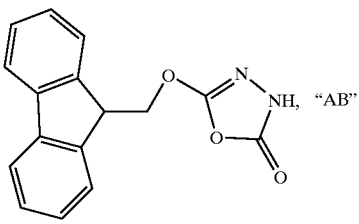

58 mg; IR (KBr): 3300s, 1780s, 1650s, 1451m, 1426m, 1347m, 1224m, 918m, 758w, 740m cm$^{-1}$.

2. Resin-bonded Fmoc-β-Phe-OH ("BC")

2.0 g of trityl chloride polystyrene resin (theoretical load 1.8 mmol) are washed in 20 ml of DMF. The resin is then admixed with a solution of 2.7 mmol Fmoc-β-Phe-OH and 2.25 mmol DIPEA in 20 ml of DMF, the mixture is shaken at room temperature for 2 hours and 1 ml of methanol is then added. The mixture is washed with DCM (5×20 ml) and methanol (3×20 ml) and dried

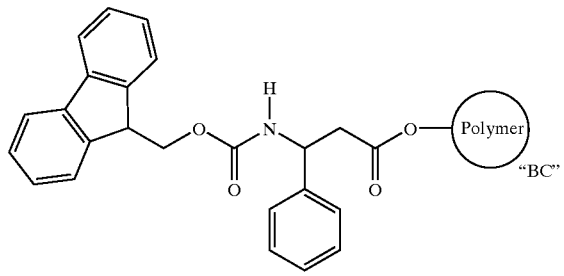

3. Resin-bonded Fmoc-azaGly-β-Phe("CD")

0.48 mmol/g of "BC" is washed with DCM (2×7 ml) and NMP (1×7 ml) and then deprotected twice using 20% piperidine in 7 ml of DMF, first for 5 min and then for 15 min. The deprotected resin is washed with NMP (5×7 ml) and absolute DCM (5×7 ml), admixed with a solution of 0.72 mmol "AB" in 7 ml of DCM and shaken at room temperature for 90 min.

The resin is washed with DCM (5×7 ml) and NMP (5×7 ml) and dried

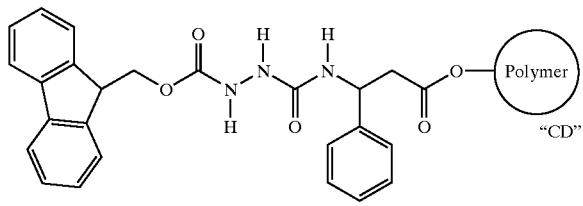

4. 3-[4-(3-Guanidinobenzoyl)semicarbazido]-3-phenylpropionic Acid 0.24 mmol of "CD" is washed with NMP (7×5 ml) and deprotected twice with 20% piperidine in 7 ml of DMF, first for 5 min and then for 15 min. The resin is then washed with NMP (5×7 ml) and DMF (2×7 ml), admixed with a solution of 0.48 mmol of 3-(9H-fluoren-9-ylmethoxycarbonylamino) benzoic acid, 0.48 mmol of HATU and 2.4 mmol of collidine in 5 ml of DMF and shaken at room temperature for 90 min. The resin is washed and deprotected as described.

The resin is subsequently admixed with a solution of 2.4 mmol of N,N'-bis-BOC-1-guanylpyrazole ("DE") in 4 ml of chloroform and left at 500 for 16 hours. The resin is washed with DCM, methanol and diethyl ether. To remove the BOC groups, the resin is shaken with a mixture of 95% TFA and 5% triisopropylsilane (5 ml) at room temperature, first for 90 min and then for 30 min. Removal of the solvent and purification by preparative RP-HPLC gives 3-[4-(3-guanidinobenzoyl)semicarbazido]-3-phenylpropionic acid, trifluoroacetate.

RT=19.1 (0→50% B, 30 min); MS (ESI): m/e=385.1 ([M+H]$^+$).

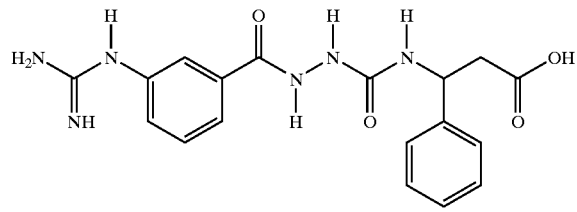

EXAMPLE 2

1. Analogously to Example 1, reaction of "CD" with 3-(9H-fluoren-9-ylmethoxycarbonylamino)phenylacetic acid followed by removal of the Fmoc group and reaction with "DE", removal of the BOC group and cleavage from the resin gives 3-[4-(3-guanidinophenylacetyl)semicarbazido]-3-phenylpropionic acid, trifluoroacetate.

RT=4.3 (10→50% B, 30 min); MS (ESI): m/e=399.1 ([M+H]$^+$).

2. Analogously to Example 1, reaction of "EF", prepared by reaction of "AB" with resin-bonded Fmoc-protected β-(4-chlorophenyl)alanine

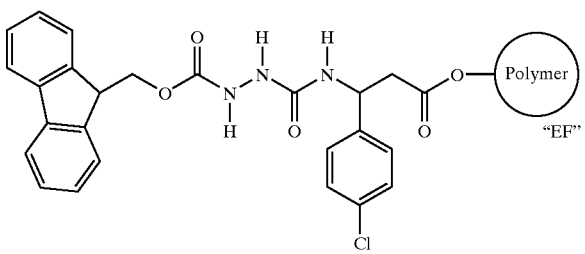

with 3-(9H-fluoren-9-ylmethoxycarbonylamino)benzoic acid followed by removal of the Fmoc group and reaction with "DE", removal of the BOC group and cleavage from the resin gives 3-[4-(3-guanidinophenylacetyl)semicarbazido]-3-(4-chlorophenyl)propionic acid, trifluoroacetate.

RT=22.8 (0→50% B, 30 min); MS (ESI): m/e=419.0 ([M+H]$^+$).

EXAMPLE 3

0.24 mmol of "CD" is washed with NMP (7×5 ml) and deprotected twice with 20% piperidine in 7 ml of DMF, first for 5 min and then for 15 min. The resin is then washed with NMP (5×7 ml) and DMF (2×7 ml), admixed with a solution of 0.48 mmol of 3-(9H-fluoren-9-ylmethoxycarbonylamino) valeric acid, 0.48 mmol of HATU and 2.4 mmol of collidine in 5 ml of DMF and shaken at room temperature for 90 min. The resin is washed and deprotected as described.

The resin is subsequently admixed with a solution of 2.4 mmol of N,N'-bis-BOC-1-guanylpyrazole ("DE") in 4 ml of chloroform and left at 500 for 16 hours. The resin is washed with DCM.

To remove the BOC groups, the resin is shaken with a mixture of 95% TFA and 5% triisopropylsilane (5 ml) at room temperature, first for 90 min and then for 30 min. Removal of the solvent and purification by preparative RP-HPLC gives 3-[4-(3-guanidinopentanoyl) semicarbazido]-3-phenylpropionic acid, trifluoroacetate.

RT=18.2 (0→50% B, 30 min); MS (ESI): m/e=365.1 ([M+H]$^+$).

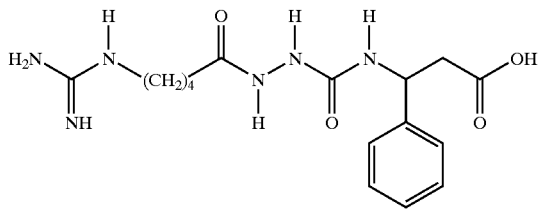

EXAMPLE 4

Analogously to Example 3, reaction of "EF" with 3-(9H-fluoren-9-ylmethoxycarbonylamino)valeric acid followed by removal of the Fmoc group, reaction with "DE" and removal of the BOC group and cleavage from the resin gives 3-[4-(3-guanidinopentanoyl)semicarbazido]-3-(4-chlorophenyl)propionic acid, trifluoroacetate.

RT=21.9 (0→50% B, 30 min); MS (ESI): m/e=399.1 ([M+H]$^+$).

EXAMPLE 5

0.60 mmol of "EF" is washed with 20 ml of NMP and deprotected twice with 20% piperidine in 20 ml of DMF, first for 5 min and then for 15 min. The resin is then washed with NMP (5×20 ml) and DMF (2×20 ml), admixed with a solution of 0.90 mmol of N-(2-(4-methylpyridyl)-5-aminovaleric [sic] acid, 0.90 mmol of HATU and 6.0 mmol of collidine in 5 ml of DMF and shaken at room temperature overnight. The resin is washed with DMF, NMP and DCM. To cleave the washed resin from the solid phase, it is shaken with 20 ml of a mixture of DCM/acetic acid/trifluoroethanol (3:1:1) at room temperature, first for 90 min and then for 30 min.

Removal of the solvent gives 3-{4-[5-(4-methylpyrid-2-ylamino)pentanoyl]semicarbazido}-3-(4-chlorophenyl) propionic acid, acetate.

Purification by preparative HPLC gives 3-{4-[5-(4-methylpyrid-2-ylamino)pentanoyl]semicarbazido)-3-(4-chlorophenyl)propionicacid, trifluoroacetate.

RT=19.3 (10→60% B, 30 min); MS (ESI): m/e=448.1 ([M+H]$^+$).

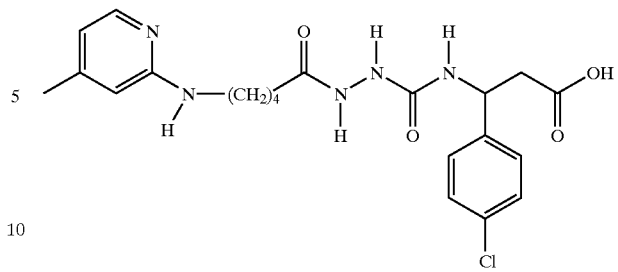

EXAMPLE 6

1. Analogously to Example 5, reaction of "FG", prepared by reaction of "AB" with resin-bonded Fmoc-protected β-(3,5-dichlorophenyl)alanine

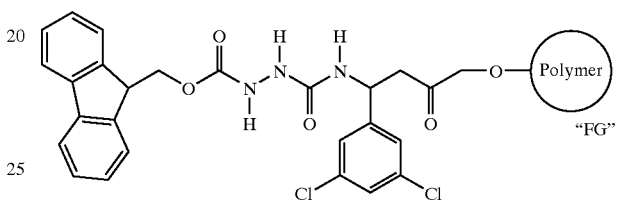

with N-(2-(4-methylpyridyl)-5-aminovaleric [sic] acid, and cleavage from the resin, gives 3-(4-[5-(4-methylpyrid-2-ylamino)pentanoyl] semicarbazido}-3-(3,5-dichlorophenyl)propionic acid, acetate.

Purification by preparative HPLC gives 3-{4-[5-(4-methylpyrid-2-ylamino)pentanoyl]semicarbazido}-3-(3,5-dichlorophenyl)propionic acid, trifluoroacetate.

RT=19.3 (0→60% B, 30 min); MS (ESI): m/e=483.4 ([M+H]$^+$).

If the reaction solution is, after cleavage from the resin and after removal of the solid phase by filtration, acidified to pH 4.0 using hydrochloric acid, the inner salt of 3-{4-[5-(4-methylpyrid-2-ylamino)pentanoyl]semicarbazido}-3-(3,5-dichlorophenyl)propionic acid is formed.

RT=19.2 (0→60% B, 30 min.)

2. Analogously to Example 5, reaction of "GH", prepared by reaction of "AB" with resin-bonded Fmoc-protected β-(3-nitrophenyl)alanine

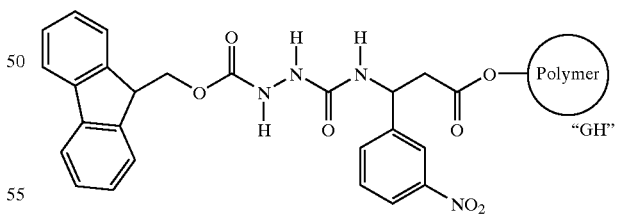

with N-(2-(4-methylpyridyl)-5-aminovaleric [sic] acid, and cleavage from the resin, gives 3-{4-[5-(4-methylpyrid-2-ylamino)pentanoyl] semicarbazido}-3-(3-nitrophenyl)propionic acid, acetate.

Purification by preparative HPLC gives 3-{4-[5-(4-methylpyrid-2-ylamino)pentanoyl]semicarbazido}-3-(3-nitrophenyl)propionic acid, trifluoroacetate.

RT=14.9 (0→60% B, 30 min); MS (ESI): m/e=459.5 ([M+H]$^+$).

3. Analogously to Example 5, reaction of "HK", prepared by reaction of "AB" with resin-bonded Fmoc-protected β-(4-fluorophenyl)phenylalanine

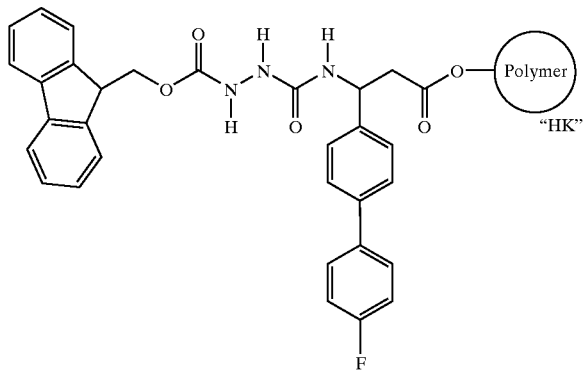

with N-(2-(4-methylpyridyl)-5-aminovaleric [sic] acid, and cleavage from the resin, gives 3-{4-[5-(4-methylpyrid-2-ylamino)pentanoyl]semicarbazido}-3-(4'-(4-fluoro)biphenyl)propionic acid, acetate.

Purification by preparative HPLC gives 3-{4-[5-2(4-methylpyrid-2-ylamino)pentanoyl]semicarbazido}-3-(4'-(4-fluoro)biphenyl)propionic acid, trifluoroacetate.

4. Analogously to Example 5, reaction of "KL", prepared by reaction of "AB" with resin-bonded Fmoc-protected β-(2-nitrophenyl)alanine

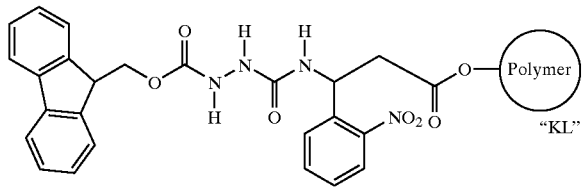

with N-(2-(4-methylpyridyl)-5-aminovaleric [sic] acid, and cleavage from the resin, gives 3-{4-[5-(4-methylpyrid-2-ylamino)pentanoyl]semicarbazido}-3-(2-nitrophenyl)propionic acid, acetate.

Purification by preparative HPLC gives 3-{4-[5-(4-methylpyrid-2-ylamino)pentanoyl]semicarbazido}-3-(2-nitrophenyl)propionic acid, trifluoroacetate.

RT=14.7 (0→60% B, 30 min); MS (ESI): m/e=459.5 ([M+H]$^+$).

5. Analogously to Example 5, reaction of "LM", prepared by reaction of "AB" with resin-bonded Fmoc-protected β-(4-trifluoromethoxyphenyl)alanine

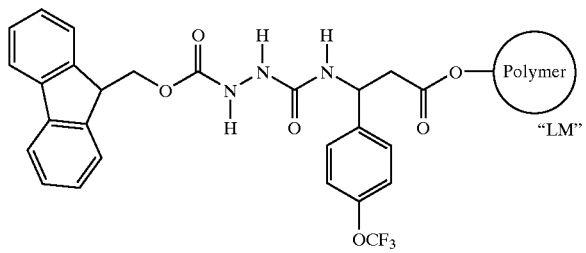

with N-(2-(4-methylpyridyl)-5-aminovaleric [sic] acid, and cleavage from the resin, gives 3-{4-[5-(4-methylpyrid-2-ylamino)pentanoyl]semicarbazido}-3-(4-trifluoromethoxyphenyl)propionic acid, acetate.

Purification by preparative HPLC gives 3-{4-[5-(4-methylpyrid-2-ylamino)pentanoyl]semicarbazido}-3-(4-trifluoromethyoxyphenyl)propionic acid, trifluoroacetate.

RT=19.8 (0→60% B, 30 min); MS (ESI): m/e=498.5 ([M+H]$^+$).

EXAMPLE 7

Analogously to Example 1.2, reaction of trityl chloride polystyrene resin with Fmoc-protected 3-aminopropionic acid gives the resin "LO"

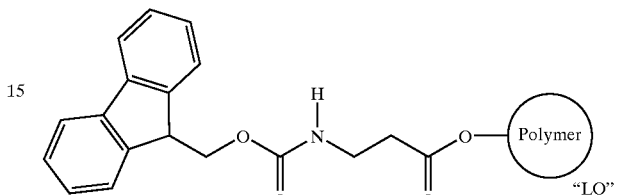

which is deprotected analogously to Example 1.3 and reacted with "AB" to give "MN"

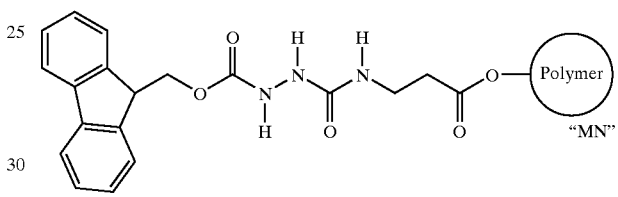

Analogously to Example 5, "MN" is reacted with N-(2-(4-methylpyridyl)-5-aminovaleric [sic] acid. After cleavage from the resin, 3-{4-[5-(4-methylpyrid-2-ylamino)pentanoyl]semicarbazido}-3-propionic acid, acetate, is obtained.

Purification by preparative HPLC gives 3-{4-[5-(4-methylpyrid-2-ylamino)pentanoyl]semicarbazido}-3-propionic acid, trifluoroacetate.

RT=7.3 (0→60% B, 30 min); MS (ESI): m/e=338.4 ([M+H]$^+$).

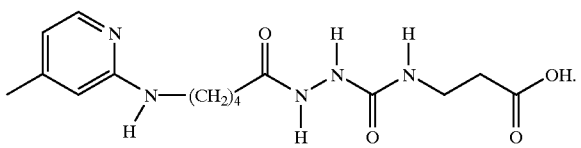

EXAMPLE 8

1. 3-Phenylglutaric Anhydride 10 mmol of 3-phenylglutaric acid and 30 mmol of acetic anhydride are heated under reflux until they have dissolved completely. After cooling, 3 ml of diethyl ether are added and the precipitate is filtered off and washed with diethyl ether. This gives 3-phenylglutaric anhydride.

$^1$H-NMR (250 MHz, CDCl$_3$): δ=2.85 (dd, 2H, CH(HCH)$_2$), 3.1 (dd, 2H, CH(CHH)$_2$), 3.4 (m, 1H, CH(CH$_2$)$_2$), 7.15–7.45 (m, 5H, arom. H).

2. 5-[N'-(9H-Fluoren-9-ylmethoxycarbonyl) hydrazino]-5-oxo-3-phenylpentanoic Acid 2.0 mmol of 3-phenylglutaric anhydride and 2.0 mmol of Fmoc-hydrazine are dissolved in 30 ml of THF and heated under reflux for 16 hours. The product is then extracted with 50 ml of DCM and 50 ml of 1N HCl solution and the organic phase is dried with MgSO₄ and filtered off. Removal of the solvent gives 5-[N'-(9H-fluoren-9-ylmethoxycarbonyl) hydrazino]-5-oxo-3-phenylpentanoic acid.

RT=10.4 (30→80% B, 30 min); MS (ESI): m/e=910.8 ([2M+Na]⁺).

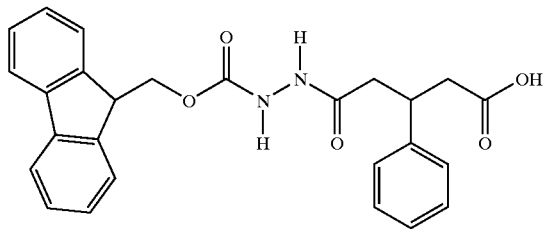

3. 5-[N'-(3-Guanidinobenzoyl)hydrazino]-5-oxo-3-phenylpentanoic Acid

5-[N'-(9H-fluoren-9-ylmethoxycarbonyl)hydrazino]-5-oxo-3-phenylpentanoic acid is deprotected analogously to the method described in Example 1. The deprotected compound is then admixed with a solution of 2.0 mmol of N,N'-bis-BOC-1-guanylpyrazole ("DE") in 4 ml of chloroform and left at 50° for 16 hours. The solvent is removed under reduced pressure. To remove the BOC groups, the residue is stirred with a mixture of 95% TFA and 5% triisopropylsilane (5 ml) at room temperature, first for 90 min and then for 30 min. Removal of the solvent and purification by preparative RP-HPLC give 5-[N'-(3-guanidinobenzoyl)hydrazino]-5-oxo-3-phenylpentanoic acid, trifluoroacetate.

RT=17.0 (10→50% B, 30 min); MS (ESI): m/e=384.1 ([M+H]⁺).

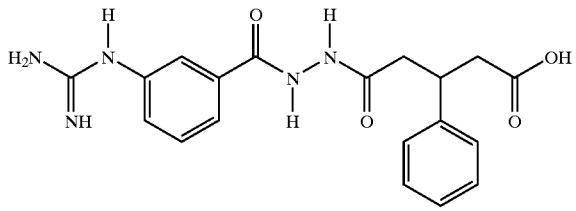

EXAMPLE 9

1. Analogously to Example 5, reaction of 5-[N'-(9H-fluoren-9-ylmethoxycarbonyl)hydrazino]-5-oxo-3-phenylpentanoic acid with N-(2-(4-methylpyridyl)-5-aminovaleric [sic] acid gives 4-{N'-[5-(4-methylpyrid-2-ylamino)pentanoyl] hydrazinocarbonyl}-3-phenylbutyric acid, acetate.

RT=22.1 (10→60% B, 30 min); MS (ESI): m/e=413.1 ([M+H]⁺).

2. Analogously to Example 5, reaction of (3R)-5-[N'-(9H-fluoren-9-ylmethoxycarbonyl)hydrazino]-5-oxo-3-(4-chlorophenyl)pentanoic acid with N-(2-(4-methylpyridyl)-5-aminovaleric [sic] acid gives (3R)-4-{N'-[5-(4-methylpyrid-2-ylamino)pentanoyl] hydrazinocarbonyl}-3-(4-chlorophenyl)butyric acid, acetate.

MS (FAB): m/e=447.9 ([M+H]⁺).

If the reaction solution is, after cleavage from the resin and after removal of the solid phase by filtration, acidified to pH 4.0 using hydrochloric acid, the inner salt of (3R)-4-{N'-[5-(4-methylpyrid-2-ylamino)pentanoyl] hydrazinocarbonyl}-3-(4-chlorophenyl)butyric acid is formed.

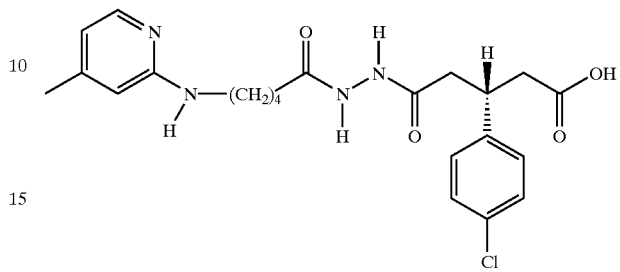

EXAMPLE 10

Analogously to Example 3, reaction of 5-[N'-(9H-fluoren-9-ylmethoxycarbonyl)hydrazino]-5-oxo-3-(4-chlorophenyl) pentanoic acid with 3-(9H-fluoren-9-ylmethoxycarbonylamino)valeric acid, followed by removal of the Fmoc group, reaction with "DE" and removal of the BOC group, gives 4-[N'-(5-guanidinopentanoyl)hydrazinocarbonyl]-3-phenylbutyric acid, trifluoroacetate.

RT=19.4 (0→50% B, 30 min); MS (ESI): m/e=364.2 ([M+H]⁺).

EXAMPLE 11

Analogously to Example 5, reaction of 5-[N'-(9H-fluoren-9-ylmethoxycarbonyl)hydrazino]-5-oxopentanoic acid, prepared analogously to Example 8.2 by reacting glutaric anhydride with Fmoc-hydrazine, with N-(2-(4-methylpyridyl)-5-aminovaleric [sic] acid gives 4-{N'-[5-(4-methylpyrid-2-ylamino)pentanoyl] hydrazinocarbonyl}butyric acid, acetate.

MS (ESI): m/e=337.4 ([M+H]⁺).

EXAMPLE 12

1. Analogously to Example 5, reaction of "NO", prepared by reaction of "AB" with resin-bound Fmoc-protected β-(4-bromophenyl)alanine,

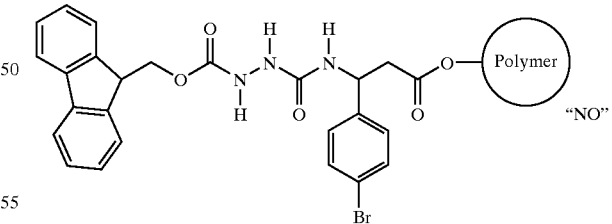

with N-(2-(4-methylpyridyl)-5-aminovaleric [sic] acid and cleavage from the resin gives 3-{4-[5-(4-methylpyrid-2-ylamino)pentanoyl] semicarbazido}-3-(4-bromophenyl)propionic acid, acetate.

Preparative HPLC gives 3-{4-5-(4-methylpyrid-2-ylamino)pentanoyl]semicarbazido}-3-(4-bromophenyl) propionic acid, trifluoroacetate.

RT=17.0 (0→60% B, 30 min.); MS (ESI): m/e=493.4 ([M+H]⁺).

2. Analogously to Example 5, reaction of "OP", prepared by reaction of "AB" with resin-bound Fmoc-protected β-(naphthalen-1-yl)alanine,

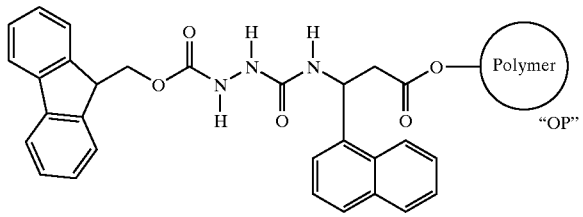

with N-(2-(4-methylpyridyl)-5-aminovaleric [sic] acid and cleavage from the resin gives 3-{4-[5-(4-methylpyrid-2-ylamino)pentanoyl]semicarbazido}-3-(naphthalin-1-yl)propionic acid, acetate.

Preparative HPLC gives 3-{4-[5-(4-methylpyrid-2-ylamino)pentanoyl]semicarbazido}-3-(naphthalin-1-yl)propionic acid, trifluoroacetate.

RT=17.6 (0→60% B, 30 min.); MS (ESI): m/e=464.5 ([M+H]$^+$).

EXAMPLE 13

1. Analogously to Example 1, reaction of "LM", prepared by reaction of "AB" with resin-bound Fmoc-protected β-(4-trifluoromethoxyphenyl)alanine,

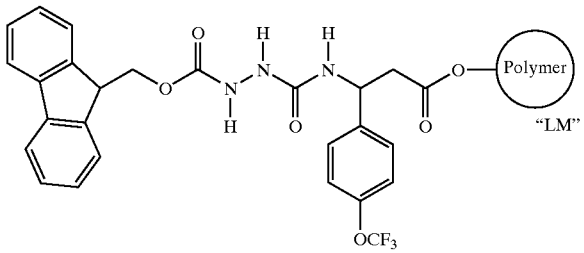

with 3-(9H-fluoren-9-ylmethoxycarbonylamino)benzoic acid, followed by removal of the Fmoc group and reaction with "DE" and removal of the BOC group and cleavage from the resin gives 3-[4-(3-guanidinobenzoyl)semicarbazido]-3-(4-trifluoromethoxyphenyl)propionic acid, trifluoroacetate.

RT=17.6 (0→60% B, 30 min.); MS (ESI): m/e=468.5 ([M+H]$^+$).

EXAMPLE 14

1. Analogously to Example 1, reaction of "FG" with 3-(9H-fluoren-9-ylmethoxycarbonylamino)benzoic acid, followed by removal of the Fmoc group and reaction with "DE" and removal of the BOC group and cleavage from the resin gives 3-[4-(3-guanidinobenzoyl)semicarbazido]-3-(3,5-dichlorophenyl)propionic acid, trifluoroacetate.

RT=17.0 (0→60% B, 30 min.); MS (ESI): m/e=454.3 ([M+H]$^+$).

2. Analogously to Example 1, reaction of "OP" with 3-(9H-fluoren-9-ylmethoxycarbonylamino)benzoic acid, followed by removal of the Fmoc group and reaction with "DE" and removal of the BOC group and cleavage from the resin gives 3-[4-(3-guanidinobenzoyl)semicarbazido]-3-naphthylpropionic acid, trifluoroacetate, RT=15.9 (0→60% B, 30 min.); MS (ESI): m/e=435.5 ([M+H]$^+$).

3. Analogously to Example 1, reaction of "NO" with 3-(9H-fluoren-9-ylmethoxycarbonylamino)benzoic acid, followed by removal of the Fmoc group and reaction with "DE" and removal of the BOC group and cleavage from the resin gives 3-[4-(3-guanidinobenzoyl)semicarbazido]-3-(4-bromophenyl)propionic acid, trifluoroacetate.

RT=14.9 (0→60% B, 30 min.); MS (ESI): m/e=464.3 ([M+H]$^+$).

4. Analogously to Example 5, reaction of "CD" with N-(2-(4-methylpyridyl)-5-aminovaleric [sic] acid and cleavage from the resin gives 3-{4-[5-(4-methylpyrid-2-ylamino)pentanoyl]semicarbazido}-3-phenylpropionic acid, acetate.

Preparative HPLC gives 3-{4-[5-(4-methylpyrid-2-ylamino)pentanoyl]semicarbazido}-3-phenylpropionic acid, trifluoroacetate.

RT=13.2 (0→60% B, 30 min.); MS (ESI): m/e=414.5 ([M+H]$^+$).

EXAMPLE 15

1. Analogously to Example 9, reaction of 5-[N'-(9H-fluoren-9-ylmethoxycarbonyl)hydrazino]-5-oxo-3-(4-bromophenyl)pentanoic acid, prepared by reaction of 3-(4-bromophenyl)glutaric anhydride with Fmoc-hydrazine, with N-(2-(4-methylpyridyl)-5-aminovaleric acid gives 3-(4-bromophenyl)-4-{N'-[5-(4-methylpyrid-2-ylamino)pentanoyl]hydrazinocarbonyl}butyric acid, acetate.

Preparative HPLC gives 3-(4-bromophenyl)-4-{N'-[5-(4-methylpyrid-2-ylamino)pentanoyl]hydrazinocarbonyl}butyric acid, trifluoroacetate.

RT=17.0 (0→60% B, 30 min.); MS (ESI): m/e=492.4 ([M+H]$^+$).

2. Analogously to Example 8, reaction of 5-[N'-(9H-fluoren-9-ylmethoxycarbonyl)hydrazino]-5-oxo-3-(4-bromophenyl)pentanoic acid with "DE" gives 3-(4-bromophenyl)-5-{N'-[1-(3-guanidinophenyl)methanoyl]hydrazino}-5-oxopentanoic acid, trifluoroacetate.

RT=15.0 (0→60% B, 30 min.); MS (ESI): m/e=463.3 ([M+H]$^+$).

3. Analogously to Example 1, reaction of 5-[N'-(9H-fluoren-9-ylmethyoxycarbonyl)hydrazino]-5-oxo-3-(4-bromophenyl)pentanoic acid with 3-(9H-fluoren-9-ylmethoxycarbonylamino)benzoic acid and naphthalen-2-ylmethyl thioacetimidate gives 5-[N'-{1-(3-acetimidoylaminophenyl)methanoyl]hydrazino}-3-(4-bromophenyl)-5-oxopentanoic [sic] acid, trifluoroacetate.

RT=15.4 (0→60% B, 30 min.); MS (ESI): m/e=462.3 ([M+H]$^+$).

EXAMPLE 16

1. Analogously to Example 9, reaction of 5-[N'-(9H-fluoren-9-ylmethoxycarbonyl)hydrazino]-5-oxo-3-(4-fluorophenyl)pentanoic acid, prepared by reaction of 3-(4-fluorophenyl)glutaric anhydride with Fmoc-hydrazine, with N-(2-(4-methylpyridyl)-5-aminovaleric [sic] acid gives 3-(4-fluorophenyl)-4-{N'-[5-(4-methylpyrid-2-ylamino)pentanoyl]hydrazinocarbonyl}butyric acid, acetate.

Preparative HPLC gives 3-(4-fluorophenyl)-4-{N'-[5-(4-methylpyrid-2-ylamino)pentanoyl]hydrazinocarbonyl} butyric acid, trifluoroacetate.

RT=14.1 (0→60% B, 30 min.); MS (ESI): m/e=431.5 ([M+H]⁺).

2. Analogously to Example 8, reaction of 5-[N'-(9H-fluoren-9-ylmethoxycarbonyl)hydrazino]-5-oxo-3-(4-fluorophenyl)pentanoic acid with "DE" gives 3-(4-fluorophenyl)-5-{N'-[1-(3-guanidinophenyl) methanoyl]hydrazino}-5-oxopentanoic acid, trifluoroacetate.

RT=11.2 (0→60% B, 30 min.); MS (ESI): m/e=402.4 ([M+H]⁺).

3. Analogously to Example 1, reaction of 5-[N'-(9H-fluoren-9-ylmethoxycarbonyl)hydrazino]-5-oxo-3-(4-fluorophenyl)pentanoic acid with 3-(9H-fluoren-9-ylmethoxycarbonylamino)benzoic acid and naphthalen-2-ylmethyl thioacetimidate gives 5-{N'-[1-(3-acetimidoylaminophenyl)methanoyl] hydrazino}-3-(4-fluorophenyl)-5-oxopentanoic acid, trifluoroacetate.

RT=12.0 (0→60% B, 30 min.); MS (ESI): m/e=401.4 ([M+H]⁺).

EXAMPLE 17

1. Analogously to Example 9, reaction of 5-[N'-(9H-fluoren-9-ylmethoxycarbonyl)hydrazino]-5-oxo-3-(4-chlorophenyl)pentanoic acid, prepared by reaction of 3-(4-chlorophenyl)glutaric anhydride with Fmoc-hydrazine, with N-(2-(4-methylpyridyl)-5-aminovaleric [sic] acid gives 3-(4-chlorophenyl)-4-{N'-[5-(4-methylpyrid-2-ylamino) pentanoyl]hydrazinocarbonyl}butyric acid, acetate, Preparative HPCL gives 3-(4-chlorophenyl)-4-{N'-[5-(4-methylpyrid-2-ylamino)pentanoyl] hydrazinocarbonyl}butyric acid, trifluoroacetate.

RT=16.3 (0→60% B, 30 min.); MS (ESI): m/e=447.9 ([M+H]⁺).

2. Analogously to Example 8, reaction of 5-[N'-(9H-fluoren-9-ylmethoxycarbonyl)hydrazino]-5-oxo-3-(4-chlorophenyl)pentanoic acid with "DE" gives 3-(4-chlorophenyl)-5-{N'-[1-(3-guanidinophenyl) methanoyl]hydrazino}-5-oxopentanoic acid, trifluoroacetate, RT=13.9 (0→60% B, 30 min.); MS (ESI): m/e=418.9 ([M+H]⁺).

3. Analogously to Example 1, reaction of 5-[N'-(9H-fluoren-9-ylmethoxycarbonyl)hydrazino]-5-oxo-3-(4-chlorophenyl)pentanoic acid with 3-(9H-fluoren-9-ylmethoxycarbonylamino)benzoic acid and naphthalen-2-ylmethyl thioacetimidate gives 5-{N'-[1-(3-acetimidoylaminophenyl)methanoyl] hydrazino}-3-(4-chlorophenyl)-5-oxopentanoic acid, trifluoroacetate, MS (ESI): m/e=417.9 ([M+H]⁺).

4. Analogously to Example 3, reaction of 5-[N'-(9H-fluoren-9-ylmethoxycarbonyl)hydrazino]-5-oxo-3-(4-chlorophenyl)pentanoic acid with 3-(9H-fluoren-9-ylmethoxycarbonylamino)valeric acid and "DE" gives 3-(4-chlorophenyl)-5-[N'-(5-guanidinopentanoyl)hydrazino]-5-oxopentanoic acid, trifluoroacetate, RT=13.7 (0→60% B, 30 min.); MS (ESI): m/e=398.5 ([M+H]⁺).

EXAMPLE 18

1. Analogously to Example 9, reaction of 5-[N'-(9H-fluoren-9-ylmethoxycarbonyl)hydrazino]-5-oxo-3-(3,5-dichlorophenyl)pentanoic acid, prepared by reaction of 3-(3,5-dichlorophenyl)glutaric anhydride with Fmoc-hydrazine, with N-(2-(4-methylpyridyl)-5-aminovaleric [sic] acid gives 3-(3,5-dichlorophenyl)-4-{N'-[5-(4-methylpyrid-2-ylamino)pentanoyl]hydrazinocarbonyl}butyric acid, acetate.

Preparative HPLC gives 3-(3,5-dichlorophenyl)-4-{N'-[5-(4-methylpyrid-2-ylamino)pentanoyl] hydrazinocarbonyl}butyric acid, trifluoroacetate.

RT=18.7 (0→60% B, 30 min.); MS (ESI): m/e=482.4 ([M+H]⁺).

2. Analogously to Example 8, reaction of 5-[N'-(9H-fluoren-9-ylmethoxycarbonyl)hydrazino]-5-oxo-3-(3,5-dichlorophenyl)pentanoic acid with "DE" gives 3-(3,5-dichlorophenyl)-5-{N'-[1-(3-guanidinophenyl) methanoyl]hydrazino}-5-oxopentanoic acid, trifluoroacetate RT=17.7 (0→60% B, 30 min.); MS (ESI): m/e=453.3 ([M+H]⁺).

3. Analogously to Example 1, reaction of 5-[N'-(9H-fluoren-9-ylmethoxycarbonyl)hydrazino]-5-oxo-3-(3,5-dichlorophenyl)pentanoic acid with 3-(9H-fluoren-9-ylmethoxycarbonylamino)benzoic acid and naphthalen-2-ylmethyl thioacetimidate gives 5-{N'-[1-(3-acetimidoylaminophenyl)methanoyl] hydrazino}-3-(3,5-dichlorophenyl)-5-oxopentanoic acid, trifluoroacetate.

RT=16.6 (0→60% B, 30 min.); MS (ESI): m/e=452.3 ([M+H]⁺).

4. Analogously to Example 9, reaction of 5-[N'-(9H-fluoren-9-ylmethoxycarbonyl)hydrazino]-5-oxo-3-(3,5-dichlorophenyl)pentanoic acid with 3-(pyrid-2-ylamino) benzoic acid gives 3-(3,5-dichlorophenyl)-5-oxo-5-{N'-[3-(pyrid-2-ylamino)benzoyl]hydrazino}pentanoic acid, acetate.

RT=33.5 (0→60% B, 30 min.); MS (ESI): m/e=488.3 ([M+H]⁺).

5. Analogously to Example 3, reaction of 5-[N'-(9H-fluoren-9-ylmethoxycarbonyl)hydrazino]-5-oxo-3-(3,5-dichlorophenyl)pentanoic acid with 3-(9H-fluoren-9-ylmethoxycarbonylamino)valeric acid and "DE" gives 3-(3,5-dichlorophenyl)-5-[N'-(5-guanidinopentanoyl) hydrazino]-5-oxopentanoic acid, trifluoroacetate.

6. Analogously to Example 9, reaction of 5-[N'-(9H-fluoren-9-ylmethoxycarbonyl)hydrazino]-5-oxo-3-(3,5-dichlorophenyl)pentanoic acid with 4-(pyrid-2-ylamino) butyric acid gives 3-(3,5-dichlorophenyl)-5-oxo-5-{N'-[4-(pyrid-2-ylamino)butanoyl]hydrazino]pentanoic acid, acetate.

Preparative HPLC gives 3-(3,5-dichlorophenyl)-5-oxo-5-{N'-[4-(pyrid-2-ylamino)butanoyl]hydrazino}oxopentanoic acid, trifluoroacetate 7. Analogously to Example 9, reaction of 5-[N'-(9H-fluoren-9-ylmethoxycarbonyl)hydrazino]-5-oxo-3-(3,5-dichlorophenyl)pentanoic acid with 4-(1H-imidazol-2-ylamino)butyric acid gives 3-(3,5-dichlorophenyl)-5-oxo-5-{N'-[4-(1H-imidazol-2-ylamino)butanoyl]hydrazino]pentanoic acid, acetate.

Preparative HPLC gives 3-(3,5-dichlorophenyl)-5-oxo-5-{N'-[4-(1H-imidazol-2-ylamino)butanoyl]hydrazino] pentanoic acid, trifluoroacetate.

MS (ESI): m/e=443.3 ([M+H]⁺).

EXAMPLE 19

1. Analogously to Example 9, reaction of 5-[N'-(9H-fluoren-9-ylmethoxycarbonyl)hydrazino]-5-oxo-3-(biphenyl-4-yl)pentanoic acid, prepared by reaction of 3-(biphenyl-4-yl)glutaric anhydride with Fmoc-hydrazine, with N-(2-(4-methylpyridyl)-5-aminovaleric [sic] acid gives 3-(biphenyl-4-yl)-4-{N'-[5-(4-methylpyrid-2-ylamino)pentanoyl]hydrazinocarbonyl}butyric acid, acetate.

RT=20.3 (0→60% B, 30 min.); MS (ESI): m/e=489.6 ([M+H]$^+$).

2. Analogously to Example 8, reaction of 5-[N'-(9H-fluoren-9-ylmethoxycarbonyl)hydrazino]-5-oxo-3-(biphenyl-4-yl)pentanoic acid with "DE" gives 3-biphenyl-4-yl-5-{N'-[1-(3-guanidinophenyl)methanoyl]hydrazino}-5-oxopentanoic acid, trifluoroacetate.

RT=19.3 (0→60% B, 30 min.); MS (ESI): m/e=460.5 ([M+H]$^+$).

3. Analogously to Example 1, reaction of 5-[N'-(9H-fluoren-9-ylmethoxycarbonyl)hydrazino]-5-oxo-3-(biphenyl-4-yl)pentanoic acid with 3-(9H-fluoren-9-ylmethoxycarbonylamino)benzoic acid and naphthalen-2-ylmethyl thioacetimidate gives 5-{N'-[1-(3-acetimidoylaminophenyl)methanoyl]hydrazino}-3-biphenyl-4-yl-5-oxopentanoic acid, trifluoroacetate.

RT=19.6 (0→60% B, 30 min.); MS (ESI): m/e=459.5 ([M+H]$^+$).

EXAMPLE 20

1. Analogously to Example 9, reaction of 5-[N'-(9H-fluoren-9-ylmethoxycarbonyl)hydrazino]-5-oxo-3-(3,5-dichloro-2-hydroxyphenyl)pentanoic acid, prepared by reaction of 3-(3,5-dichloro-2-hydroxyphenyl)glutaric anhydride with Fmoc-hydrazine, with 4-(pyridin-2-ylamino)butyric acid gives 3-(3,5-dichloro-2-hydroxyphenyl)-5-oxo-{5-[4-pyrid-2-ylamino)butanoyl]hydrazino}pentanoic acid, acetate.

Preparative HPLC gives 3-(3,5-dichloro-2-hydroxyphenyl)-5-oxo-5-{N'-[4-pyrid-2-ylamino)butanoyl]hydrazino}pentanoic acid, trifluoroacetate.

MS (ESI): m/e=470.3 ([M+H]$^+$).

2. Analogously to Example 9, reaction of 5-[N'-(9H-fluoren-9-ylmethoxycarbonyl)hydrazino]-5-oxo-3-(3,5-dichloro-2-hydroxyphenyl)pentanoic acid with 4-(1H-imidazol-2-ylamino)butyric acid gives 3-(3,5-dichloro-2-hydroxyphenyl)-5-oxo-5-{N'-[4-(1H-imidazol-2-ylamino)butanoyl]hydrazino}pentanoic acid, acetate.

Preparative HPLC gives 3-(3,5-dichloro-2-hydroxyphenyl)-5-oxo-5-{N'-[4-(1H-imidazol-2-ylamino)butanoyl]hydrazino}pentanoic acid, trifluoroacetate MS (ESI): m/e=459.3 ([M+H]$^+$).

EXAMPLE 21

1. Analogously to Example 9, reaction of 5-[N'-(9H-fluoren-9-ylmethoxycarbonyl)hydrazino]-5-oxo-3-(3-nitrophenyl)pentanoic acid, prepared by reaction of 3-(3-nitrophenyl)glutaric anhydride with Fmoc-hydrazine, with N-(2-(4-methylpyridyl)-5-aminovaleric [sic] acid gives 3-(3-nitrophenyl)-4-{N'-[5-(4-methylpyridin-2-ylamino)pentanoyl]hydrazinocarbonyl}butyric acid, acetate.

MS (ESI): m/e=458.5 ([M+H]$^+$).

2. Analogously to Example 8, reaction of 5-[N'-(9H-fluoren-9-ylmethoxycarbonyl)hydrazino]-5-oxo-3-(3-nitrophenyl)pentanoic acid with "DE" gives 5-{N'-[1-(3-guanidinophenyl)methanoyl]hydrazino}-3-(3-nitrophenyl)-5-oxopentanoic acid, trifluoroacetate.

RT=11.3 (0→60% B, 30 min.); MS (ESI): m/e=429.4 ([M+H]$^+$).

3. Analogously to Example 1, reaction of 5-[N'-(9H-fluoren-9-ylmethoxycarbonyl)hydrazino]-5-oxo-3-(3-nitrophenyl)pentanoic acid with 3-(9H-fluoren-9-ylmethoxycarbonylamino)benzoic acid and naphthalen-2-ylmethyl thioacetimidate gives 5-{N'-[1-(3-acetamidoylaminophenyl)methanoyl]hydrazino}-3-(3-nitrophenyl)-5-oxopentanoic acid, trifluoroacetate.

EXAMPLE 22

1. Analogously to Example 9, reaction of 5-[N'-(9H-fluoren-9-ylmethoxycarbonyl)hydrazino]-5-oxo-3-(4-methoxyphenyl)pentanoic acid, prepared by reaction of 3-(4-methoxylphenyl)glutaric anhydride with Fmoc-hydrazine, with N-(2-(4-methylpyridyl)-5-aminovaleric [sic] acid gives 3-(4-methoxyphenyl)-4-{N'-[5-(4-methylpyridin-2-ylamino)pentanoyl]hydrazinocarbonyl}butyric acid, acetate.

RT=13.7 (0→60% B, 30 min.); MS (ESI): m/e=443.4 ([M+H]$^+$).

2. Analogously to Example 8, reaction of 5-[N'-(9H-fluoren-9-ylmethoxycarbonyl)hydrazino]-5-oxo-3-(4-methoxyphenyl)pentanoic acid with "DE" gives 5-{N'-[1-(3-guanidinophenyl)methanoyl]hydrazino}-3-(4-methoxyphenyl)-5-oxopentanoic acid, trifluoroacetate.

RT=10.6 (0→60% B, 30 min.); MS (ESI): m/e=414.4 ([M+H]$^+$).

3. Analogously to Example 1, reaction of 5-[N'-(9H-fluoren-9-ylmethoxycarbonyl)hydrazino]-5-oxo-3-(4-methoxyphenyl)pentanoic acid with 3-(9H-fluoren-9-ylmethoxycarbonylamino)benzoic acid and naphthalen-2-ylmethyl thioacetimidate gives 5-N'-[1-(3-acetimidoylaminophenyl)methanoyl]hydrazino}-3-(4-methoxyphenyl)-5-oxopentanoic acid, trifluoroacetate.

RT=10.5 (0→60% B, 30 min.); MS (ESI): m/e=413.4 ([M+H]$^+$).

The examples below relate to pharmaceutical preparations:

EXAMPLE A

Injection Vials

A solution of 100 g of an active compound of the formula I and 5 g of disodium hydrogen phosphate in 3 l of doubly distilled water is brought to pH 6.5 with 2 N hydrochloric acid and subjected to sterile filtration, and injection vials are filled with the solution, which is lyophilized under sterile conditions and closed under sterile conditions. Each injection vial contains 5 mg of active compound.

EXAMPLE B

Suppositories

A mixture of 20 g of an active compound of the formula I with 100 g of soya lecithin and 1400 g of cocoa butter is melted, poured into moulds and allowed to cool. Each suppository contains 20 mg of active compound.

EXAMPLE C

Solution

A solution is prepared from 1 g of an active compound of the formula I, 9.38 g of NaH$_2$PO$_4$.2H$_2$O, 28.48 g of Na$_2$HPO$_4$.12H$_2$O and 0.1 g of benzalkonium chloride in 940 ml of doubly distilled water. It is brought to pH 6.8, topped up to 1 l and sterilized by irradiation. This solution can be used in the form of eye drops.

EXAMPLE D

Ointment 500 mg of an active compound of the formula I are mixed with 99.5 g of vaseline under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is pressed to tablets in the customary manner such that each tablet contains 10 mg of active compound.

EXAMPLE F

Coated Tablets

Tablets are pressed analogously to Example E and are then coated in the customary manner with a coating of sucrose, potato starch, talc, tragacanth and dyestuff.

EXAMPLE G

Capsules

Hard gelatin capsules are filled with 2 kg of active compound of the formula I in the customary manner such that each capsule contains 20 mg of the active compound.

EXAMPLE H

Ampoules

A solution of 1 kg of active compound of the formula I in 60 l of doubly distilled water is subjected to sterile filtration, and ampoules are filled with the solution, which is lyophilized under sterile conditions and closed under sterile conditions. Each ampoule contains 10 mg of active compound.

EXAMPLE I

Inhalation Spray 14 g of the active compound of the formula I are dissolved in 10 l of isotonic NaCl solution, and the solution is filled into customary commercial spray containers having a pump mechanism. The solution can be sprayed into mouth or nose. One squirt (approximately 0.1 ml) corresponds to a dose of approximately 0.14 mg.

What is claimed is:

1. A compound formula I

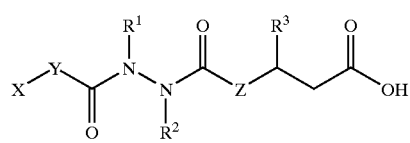

in which

X is H$_2$N—C(=NH)—NH—, H$_3$C—C(=NH)—NH or Het$^1$—NH—,

Y is

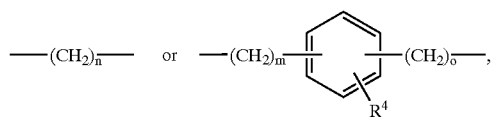

Z is is N—R$^2$ or CH—R$^2$,

R$^1$, R$^2$ are each independently of one another H or A,

R$^3$ is H, Ar or Het,

R$^4$ is H, A, Ar, OH, OA, OAr, arylalkyl, Hal, CN, NO$_2$, CF$_3$ or OCF$_3$

A is alkyl having 1 to 6 carbon atoms,

Ar is phenyl which is unsubstituted or mono-, di- or trisubstituted by A, OH, OA, CF$_3$, OCF$_3$, CN, NO$_2$ or Hal and which may be substituted by a phenyl which is mono-, di- or trisubstituted by A, OH, OA, CF$_3$, OCF$_3$, CN, NO$_2$ or Hal such that an unsubstituted or substituted biphenyl is formed, or is naphthyl which is unsubstituted or mono-, di- or unsubstituted by A, OH, OA, CF$_3$, OCF$_3$, CN, NO$_2$ or Hal, Hal is F, Cl, Br or I, Het is a saturated, partially or fully unsaturated mono- or bicyclic heterocyclic radical having 5 to 10 ring members, where 1 or 2 nitrogen and/or 1 or 2 sulfur or oxygen atoms may be present and where the heterocyclic radical may be mono or disubstituted by CN, Hal, OH, OA, CF$_3$, A, NO or OCF$_3$, Het$^1$ is a 5- or 6-membered aromatic heterocycle having 1 to 4 nitrogen atoms which may be unsubstituted or mono- or disubstituted by Hal, A, OA, Ar, OAr, arylakyl, CN NO$_2$, CF$_3$ or OCF$_3$, n is 2, 3, 4, 5 or 6, m, o are 0, 1 or 2; or a physiologically acceptable salts or solvates.

2. A compound according to claim 1, wherein said compound is a) 5-[N'-(3-guanidinobenzoyl)hydrazino]-5-oxo-3-phenylpentanoic acid or a physiologically acceptable salt or solvate thereof, b) 3-[4-(3-guanidinophenylacetyl)semicarbazido]-3-phenylpropionic acid or a physiologcally acceptable salt or solvate thereof, c) 3-[4-(3-guanidinobenzoyl)semicarbazido]-3-phenylpropioic acid or a physiologically acceptable salt or solvate thereof, d) 4-{N'-[5-(4-methylpyridin-2-ylamino)pentanoyl]hydrazinocarbonyl}-3-phenylbutyric acid or a physiologically acceptable salt or solvate thereof, e) 3-[4-(5-guanidinopentanoyl)semicarbazido]-3-phenylpropionic acid or a physiologically acceptable salt or solvate thereof, f) 4-[N'-(5-guanidinopentanoyl)hydrazinocarbonyl]-3-phenylbutyric acid or a physiologically acceptable salt or solvate thereof, g) 3-[4-(3-guanidinobenzoyl)semicarbazido]-3-(4-chlorophenyl)propionic acid or a physiologically acceptable salt or solvate thereof, h) 3-{4-[5-(4-methylpyridin-2-ylamino)pentanoyl]semicarbazido}-3-(4-chlorophenyl)propionic acid or a physiologically acceptable salt or solvate thereof, i) 3-[4-(5-guanidinopentanoyl)semicarbazido]-3-(4-chlorophenyl)propionic acid or a physiologcally acceptable salt or solvate thereof.

3. A process for preparing a compounds according to claim 1 comprising:
a) reacting a compound of formula II

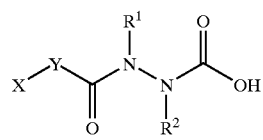

in which free amino groups are protected by a suitable amino protective group,
with a compound of formula III

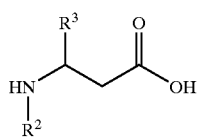

in which a free hydroxyl group is protected by a suitable hydroxyl protective group or attached to a solid phase,
and subsequently removing the protective groups and/or the solid phase;
or
b) reacting a compound of formula IV

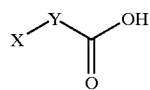

in which free amino groups are protected by a suitable amino protective group
with a compound of the formula V

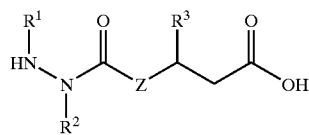

in which a free hydroxyl group is protected by a suitable hydroxyl protective group or attached to a solid phase,
and subsequently removing the protective groups and/or the solid phase;
or
c) liberating a compound of formula I from one of its functional derivatives by treatment with a solvolysing or hydrogenolysing agent,
or
d) converting a basic or acidic compound of formula I into one of its salts by treatment with an acid or base.

4. A method for inhibiting integrins in a patient comprising administering to said patient an effective amount of a compound Compounds of the formula I according to claim 1.

5. A pharmaceutical composition comprising at least one compound according to claim 1 and at least one solid, liquid, or semiliquid excipient or auxiliary.

6. A method for treating thromboses, myocardial infarction, coronary heart diseases, arteriosclerosis, inflammations, tumours, osteoporosis, an infections or restenosis after angioplasty in a patient comprising administering to said patient an effective amount of a compound according to claim 1.

7. A method for treating a pathological process in a patient which is maintained or propagated by angiogenesis comprising administering to said patient an effective amount of a compound according to claim 1.

8. A compound according to claim 1, wherein Het is 2-, 3- or 4pyridyl or 1-, 2-, 3-, 4-, 5-, 6- or 7-1H-indolyl.

9. A compound according to claim 1, wherein $Het^1$ is unsubstituted or substituted 2- or 3-pyrrolyl, 2,4- or 5-imidazolyl, 3-, 4- or 5-pyrazolyl, 2-, 3- or 4-pyridyl, 2-, 4-, 5- or 6-pyrimidinyl, 3- or 4-pyridazinyl, 2- or 3-pyrazinyl.

10. A compound according to claim 1, wherein $Het^1$—NH is pyrrol-2- or pyrrol-3-ylamine, imidazol-2-, imidazol-4- or imidazol-5-ylamine, pyrazol-3-, pyrazol-4- or pyrazol-5-ylamine, pyrid-2-, pyrid-3- or pyrid-4-ylamine, pyrimidin-2-, pyrimidin-4-, pyrimidin-5- or pyrimidin-6-ylamine, pyridazin-3- or pyridazin-4-ylamine, pyrazin-2- or pyrazin-3-ylamine, where in each case the heterocyclic ring is unsubstituted or substituted by alkyl.

11. A compound according to claim 1, wherein $Het^1$—NH is pyrid-2-ylamine, imidazol-2-ylamine or 4-methylpyridin-2-ylamine.

12. A compound according to claim 1, wherein OA is methoxy, ethoxy, propoxy, butoxy, pentyloxy or hexyloxy.

13. A compound according to claim 1, wherein $R^1$ is H or A, where A is methyl, ethyl isopropyl, n-propyl, n-butyl, isobutyl, sec-butyl or tert-butyl.

14. A compound according to claim 1, wherein $R^2$ is H or A, where A is methyl, ethyl, isopropyl n-propyl n-butyl isobutyl, sec-butyl or tert-butyl.

15. A compound according to claim 1, wherein $R^3$ is H, phenyl, p-chlorophenyl, p-bromophenyl, p-fluorophenyl, 3,5-dichlorophenyl, o- or m-nitrophenyl, p-trifluoromethoxyphenyl, p-methoxyphenyl, 3,5-dichloro-2-hydroxyphenyl, naphthalin-1-yl, biphenyl-4-yl or 4'-(4-fluorobiphenyl).

16. A compound according to claim 1, wherein $R^4$ is H and methyl.

17. A compound according to claim 1, wherein X is $H_2N$—$C(=NH)$—NH—, $H_3C$—$C(=NH)$—NH—, pyridin-2-ylamino, imidazol-2-ylamino or 4-methylpyridin-2-ylamino.

18. A compound according to claim 1, wherein Y is —$(CH_2)_n$— or

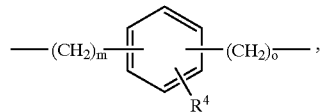

n is 3 or 4, and m is 0, 1 or 2, in particular 0, and o is 0 or 1.

19. A compound according to claim 1, wherein Z is NH or $CH_2$.

20. A compound according to claim 1, wherein X is $H_2N$—$C(=NH)$—NH—.

21. A compound according to claim 1, wherein Y is

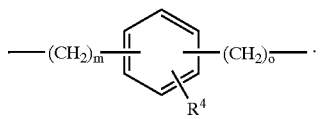

22. A compound according to claim 1, wherein Z is N—R².
23. A compound according to claim 1, wherein Z is CH—R².
24. A compound according to claim 1, wherein X is H₂N—C(=NH)—NH—, H₃C—C(=NH)—NH— or Het¹—NH— and Y is —(CH₂)ₙ—.
25. A compound according to claim 1, wherein X is H₂N—C(=NH)—NH— and Y is

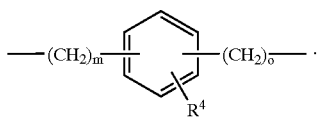

26. A compound according to claim 1, wherein X is H₂N—C(=NH)NH— or Het¹—NH—, Y is —(CH₂)ₙ—, R³ is Ar, and Z is NH.
27. A compound according to claim 1, wherein X is H₂N—C(=NH)—NH—, R³ is Ar, Z is NH and Y is

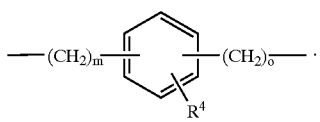

28. A compound according to claim 1, wherein X is H₂N—C(=NH)—NH—, or Het¹—NH—, R³ is Ar, Y is —(CH₂)ₙ— and Z is CH₂.
29. A compound according to claim 1, wherein X is H₂N—C(=NH)—NH—, R³ is Ar, Z is CH₂ and Y is

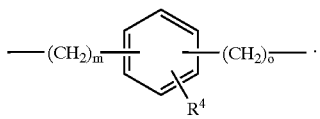

30. A compound according to claim 1, wherein X is H₂N—C(=NH)—NH—, H₃C—C(=NH)—NH— or Het¹—NH—, Z is NH or CH₂, R¹ and R² are each H, R³ is Ar, R⁴ is H, Het¹ is 4-methylpyridin-2-yl, pyridin-2-yl or imidazol-2-yl, n is 3 or 4, m is 0, o is 0 or 1, and Y is —(CH₂)ₙ— or

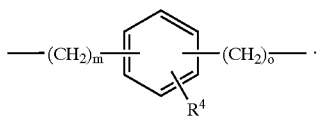

31. A compound according to claim 1, wherein X is H₂N—C(=NH)—NH—, H₃C—C(=NH)—NH— or Het¹—NH—, Z is NH or CH₂, R¹ and R² are each H, R³ is phenyl which is unsubstituted or mono-, di- or trisubstituted by OH, OA, OCF₃, NO₂ or Hal and which may be substituted by a phenyl which is unsubstituted or mono-, di- or trisubstituted by Hal such that an unsubstituted or substituted biphenyl is formed or unsubstituted naphthyl, R⁴ is H, Het¹ is 4-methylpyridin-2-yl, or pyridin-2-yl or imidazol-2-yl, n is 3 or 4, m is 0, o is 0 or 1, and Y is —(CH₂)ₙ— or

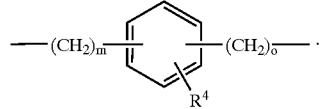

32. A compound according to claim 1, wherein X is H₂N—C(=NH)—NH— or Het¹—NH—, Z is CH₂, R¹ and R² are each H, R⁴ is H, R³ is phenyl which is unsubstituted or mono-, di- or trisubstituted by OH, OA, OCF₃, NO₂ or Hal and which may be substituted by a phenyl which is unsubstituted or mono-, di- or trisubstituted by Hal such that an unsubstituted or substituted biphenyl is formed or unsubstituted naphthyl Het¹ is 4-methylpyridin-2-yl, pyridin-2-yl or imidazol-2-yl, n is 4, m and o are 0, and Y is —(CH₂)ₙ— or

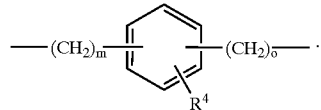

33. A compound according to claim 1, wherein R³ is unsubstituted biphenyl-4-yl or is phenyl which is mono-, di- or trisubstituted by Hal.
34. A compound according to claim 1, wherein X is H₂N—C(=NH)—NH— or Het¹—NH—, Z is CH₂, R¹ and R² are each H, R⁴ is H, R³ is phenyl which is unsubstituted or mono-, di- or trisubstituted by OH, OA, OCF₃, NO₂ or Hal and which may be substituted by a phenyl which is unsubstituted or mono-, di- or trisubstituted by Hal such that an substituted or substituted biphenyl is formed or unsubstituted naphthyl, Het¹ is 4-methylpyridin-2-yl, pyridin-2-yl or imidazol-2-yl, n is 3 or 4, m is 0, o is 0 or 1, and Y is —(CH₂)ₙ— or

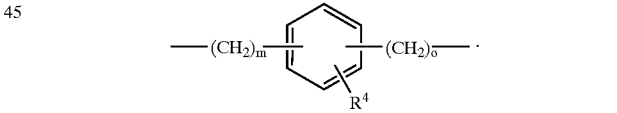

35. A compound according to claim 1, wherein X is H₂N—C(=NH)—NH— or Het¹—NH—, Z is CH₂, R¹ and R² are each H, R⁴ is H, R³ is biphenyl-4-yl, 4-chlorophenyl or 3,5-dichlorophenyl, Het¹ is 4-methylpyridin-2-yl, pyridin-2-yl or imidazol-2-yl, n is 3 or 4, m is 0, o is 0 or 1, and Y is —(CH₂)ₙ— or

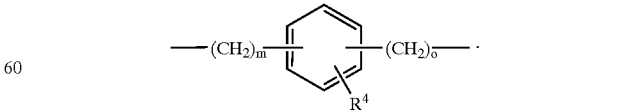

* * * * *

UNITED STATES PATENT AND TRADEMARK OFFICE
CERTIFICATE OF CORRECTION

PATENT NO. : 6,649,613 B1
DATED : November 18, 2003
INVENTOR(S) : Gunter Holzemann et al.

Page 1 of 1

It is certified that error appears in the above-identified patent and that said Letters Patent is hereby corrected as shown below:

Column 32,
Line 21, reads "unsubstituted," should read -- trisubstituted --
Line 29, reads "mono," should read -- mono- --
Line 30, reads "NO," should read -- $NO_2$ --
Line 34, reads "arylakyl, CN," should read -- arylalkyl, CN, --
Line 37, reads "salts or solvates," should read -- salt or solvate --
Lines 44 and 66, reads "physiologcally," should read -- physiologically --
Line 48, reads "phenylpropioic," should read -- phenylpropionic --

Column 33,
Line 1, reads "compounds," should read -- compound --

Column 34,
Line 3, reads "infections," should read -- infection --
Line 13, reads "4pyridyl," should read -- 4-pyridyl --
Line 15, reads "2,4-," should read -- 2-,4- --
Line 34, reads "ethyl" should read -- ethyl, --
Line 37, reads "isopropyl n-propyl n-butyl," should read -- isopropyl, n-propyl, n-butyl, --

Column 35,
Line 26, reads "C(=NH)NH--," should read -- C(=NH) --NH-- --

Column 36,
Line 21, reads "naphthyl," should read -- naphthyl, --
Line 40, reads "substituted," should read -- unsubstituted --

Signed and Sealed this

Fourteenth Day of September, 2004

JON W. DUDAS
*Director of the United States Patent and Trademark Office*